(12) United States Patent
Maier et al.

(10) Patent No.: US 8,357,653 B2
(45) Date of Patent: Jan. 22, 2013

(54) SYSTEM AND METHOD FOR INHIBITING CELLULAR PROLIFERATION WITH TACHYKININS

(76) Inventors: Nathan C. Maier, Hayward, CA (US); Amiel G. Jarstfer, Longview, TX (US)

(*) Notice: Subject to any disclaimer, the term of this patent is extended or adjusted under 35 U.S.C. 154(b) by 73 days.

(21) Appl. No.: 12/717,470

(22) Filed: Mar. 4, 2010

(65) Prior Publication Data

US 2011/0009334 A1    Jan. 13, 2011

Related U.S. Application Data

(63) Continuation of application No. 10/994,170, filed on Nov. 19, 2004, now Pat. No. 7,691,817, which is a continuation of application No. PCT/US03/16059, filed on May 24, 2003, which is a continuation-in-part of application No. 10/267,918, filed on Oct. 8, 2002, now abandoned, application No. 12/717,470, which is a continuation of application No. 09/713,299, filed on Nov. 16, 2000, now abandoned.

(60) Provisional application No. 60/383,499, filed on May 24, 2002.

(51) Int. Cl.
*A61K 38/08* (2006.01)
*A61P 17/12* (2006.01)

(52) U.S. Cl. .......................................... 514/1.1; 514/5.2

(58) Field of Classification Search ........................ None
See application file for complete search history.

(56) References Cited

U.S. PATENT DOCUMENTS

| | | | |
|---|---|---|---|
| 5,990,125 | A | 11/1999 | Howard |
| 6,103,905 | A | 8/2000 | Cuny |
| 7,119,071 | B2 | 10/2006 | Rameshwar |
| 7,425,217 | B2 | 9/2008 | Maier et al. |
| 7,691,817 | B2 | 4/2010 | Maier et al. |
| 2004/0057945 | A1 | 3/2004 | Maier et al. |

FOREIGN PATENT DOCUMENTS

| | | |
|---|---|---|
| WO | 9602509 A1 | 2/1996 |
| WO | 2004000208 A2 | 12/2003 |

OTHER PUBLICATIONS

Lipke et al.—Dec. 2006 Clinical Medicine & Research, vol. 4, No. 4, pp. 273-293.
Champagne et al.—"Sialokinin I and II: Vasodilatory Tachykinins from the Yellow Fever Mosquito Aedes Aegypti"—Proc. Natl. Acad. Sci., 1994, 91, pp. 138-142.
Beernsten et al.—"Characterization of the Sialokinin I Gene Encoding the Salivary Vasodilator of the Yellow Fever Mosquito, Aedes Aegypti"—Insect Molecular Biology, 1999, vol. 9, pp. 459-467.
Siviter et al.—Journal of Biological Chemistry, 2000, 275, pp. 23273-23280.
Palma et al.—Life Sciences, 2000, 67, pp. 985-1001.
Severini et al.—"The Tachykinin Peptide Family"—Pharmacol Rev., 2002, vol. 54, No. 2, pp. 285-322.
Gura—Science, 1997, 278, pp. 1041-1042.
Jain—Sci. Am., 1994, 271, pp. 58-65.
Curti—Crit. Rev. In Oncology/Hematology, 1993, 14, pp. 29-39.
Saunders et al.—"Simplifying the Molecular Mechanisms of Human Papillomavirus"—Sexually Transmitted Diseases, vol. 16, No. 4, pp. 823-827, Oct. 1998.
Lunberg—"Tachykinins, Sensory Nerves, and Asthma—An Overview"—Can. Journal Physiol. Pharmacol., vol. 73, pp. 908-914, 1995.
Hedge et al.—"Crystal Structure of the E2 DNA-Binding Domain From Human Papillomavirus Type 16: Implications for its DNA Bind-Site Selection Mechanism"—Journal of Molecular Biology, vol. 284, No. 5, pp. 1479-1489, Dec. 2008.
Flaitz et al.—"Molecular Piracy: The Viral Link to Carcinogenesis"—Oral Oncology, vol. 34, pp. 448-453, 1998.
Reid et al.—"Stimulation of Epithelial Cell Growth by the Neuropeptide Substance"—Journal of Cellular Biochemistry, vol. 52, 476-485, 1993.
Takebayashi et al. —"Role of Tachykinins in Airway Responses to Ozone in Rats"—Journal of Applied Physiology, vol. 85, No. 2, pp. 442-450, 1998.
Noveral et al. —"Tachykinin Regulation of Airway Smooth Muscle Cell Proliferation"—American Journal of Physiology, vol. 269, pp. L339-L343, 1995.
Klug et al.—"Chromosome Mutations: Variation in Chromosome Number and Arrangement"—Chapter 10, Concepts of Genetics, Sixth Edition, pp. 251 and pp. 262-263, Prentice Hall, Upper Saddle River, NJ, 1999.
Palma et al. —"Anti-Tumour Activity of Tachykinin NK, Receptor Antagonist on Human Glioma U373 MG Xenograft"—British Journal of Cancer, vol. 82, No. 2, pp. 480-487, 2000.
ISA/US, International Search Report, PCT/US2003/016059, issued Sep. 10, 2004.

*Primary Examiner* — Laura B Goddard
(74) *Attorney, Agent, or Firm* — John P. O'Banion

(57) ABSTRACT

Systems and methods are described providing therapeutic preparations of tachykinins, and more specifically sialokinins, for treating various types of abnormal cellular proliferation conditions in regions of tissue associated with the body of a patient. The sialokinins may be isolated and purified from natural or bioengineered sources, or may be synthesized, and may be combined into, with, or on an implant for local elution or otherwise as a powder mixed in a carrier vehicle for injection delivery. Tumors, warts, and restenosis are abnormal cellular proliferation conditions treated by therapeutic doses of sialokinin. Size of the tissue structure to be treated is used to determine the therapeutic dose of sialokinin. The sialokinins are either locally or systemically delivered at therapeutic doses for the desired effect. Implants such as stents are coated with sialokinins for local elution at the site of injury or tissue otherwise vulnerable to harmful conditions treated by the sialokinin.

12 Claims, 5 Drawing Sheets

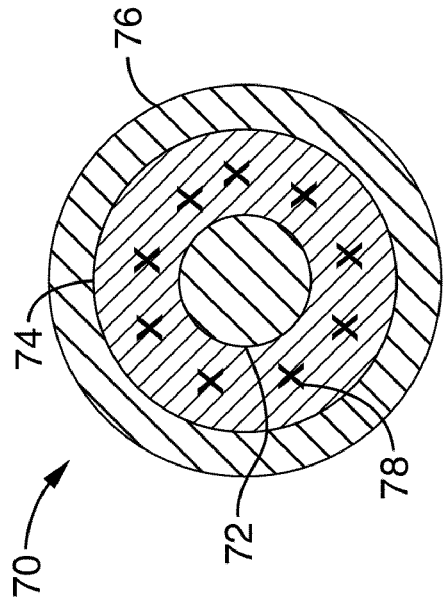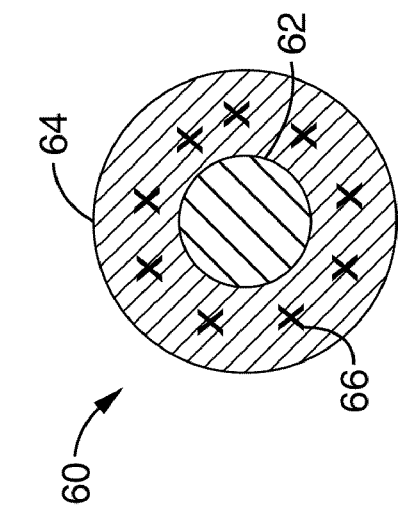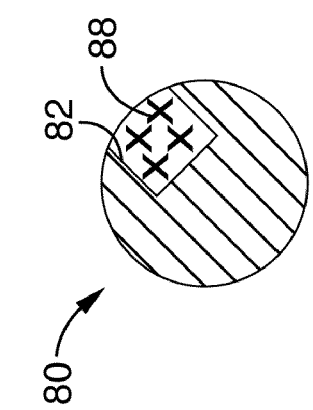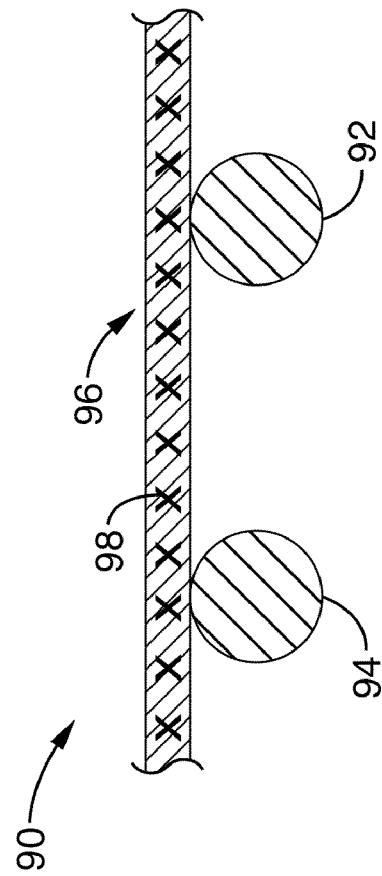

SYSTEM AND METHOD FOR INHIBITING CELLULAR PROLIFERATION WITH TACHYKININS

CROSS-REFERENCE TO RELATED APPLICATIONS

This application is a continuation of U.S. application Ser. No. 10/994,170 filed on Nov. 19, 2004, now U.S. Pat. No. 7,691,817, incorporated herein by reference in its entirety, which claims priority from, and is a 35 U.S.C. §111(a) continuation of, PCT international application serial number PCT/US03/16059 filed on May 24, 2003, incorporated herein by reference in its entirety, which claims priority from U.S. application Ser. No. 60/383,499 filed on May 24, 2002, incorporated herein by reference in its entirety. This application is a continuation-in-part of U.S. application Ser. No. 10/267,918 filed on Oct. 8, 2002 now abandoned, incorporated herein by reference in its entirety, which is a continuation of U.S. application Ser. No. 09/713,299, filed on Nov. 16, 2000 now abandoned, incorporated herein by reference in its entirety.

This application is related to U.S. application Ser. No. 10/445,400 filed on May 24, 2003, now U.S. Pat. No. 7,425,217, incorporated herein by reference in its entirety.

This application is related to PCT International Publication No. WO 2004/000208 A2 published on Dec. 31, 2003, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

This application includes a sequence listing submitted on compact disc in computer readable form that corresponds to the written sequence listing presented in the specification, which compact disc is incorporated herein by reference in its entirety. The sequence listing information recorded in computer readable form is identical to the written sequence listing.

BACKGROUND OF THE INVENTION

1. Field of the Invention

This invention pertains generally to compositions and treatments for controlling unregulated cellular proliferation in mammals, and more particularly to the preparation and use of Tachykinins, preferably Sialokinins, to modulate unwanted cellular proliferation.

2. Description of Related Art

Studies from the recent past indicate that the immune system and the nervous system are integrated forming an interdependent neuroimmune network rather than existing as independent systems. This network includes a complex array of endocrine, neurocrine, autocrine and paracrine interactions between different cell types within the two systems. The reciprocal flow of information between the nervous and immune systems uses an extensive array of mechanisms usually involving soluble signaling molecules or cell to cell contacts. The network also includes positive and negative signals as well as feed forward and feedback loops that control neuroimmune functions.

The coordination, regulation and amplification of the mammalian neuroimmune network pathways involve many different classes of molecules including neurohormones, cytokines, non-peptide mediators and neurotransmitters such as tachykinins, enkephalins and endothelins. For example, significant concentrations of neuropeptides produced by nerve cells are found at the sites of inflammation and immune reactions acting on receptors expressed on immunocytes and may be involved in the eradication of infected cells as well as modulating the proliferation of cells for repair.

Likewise, pro-inflammatory cytokines that may be released from activated macrophages or monocytes have been shown to target nervous system cells that control sleep, mood and temperature during infection.

Cytokines are a diverse group of immunomodulatory proteins that can modulate the biological activity and proliferation of cells and tissues. Unlike hormones that are produced by specialized cells or glands, cytokines are secreted proteins produced by a number of cell types in different parts of the body. Cytokines have biological activity that may be similar to some hormones but have a broader spectrum of target cells than hormones. Furthermore, almost all of the cytokines are pleiotropic in nature exhibiting multiple biological activities. Cytokines include Interlukins, Lymphokines, Monokines, Interferons, colony stimulating factors and Chemokines.

Cytokine receptors are found on the cells of both the nervous and immune systems. Molecular signals can induce or repress the synthesis of cytokines and cytokine receptors in the same cell or sequentially on different cells. Some cytokine receptor proteins have been shown to function as signal transducers within the cell as well as binding the cytokine ligand due to the tyrosine kinase activity of the receptor. It can be seen that the cytokines are important positive and negative regulators of cell survival and death, mitosis, cell transformation and cell differentiation as well as the systemic responses to infection such as inflammation.

Some viral strategies exploit the activity of various cytokines in order to evade an immune response from the host. For example, virus encoded cytokine analogs may be produced that antagonize or agonize the host cytokine receptors. The virus may produce a protein that inhibits the synthesis and release of cytokines from infected cells or interferes with the interaction between the host cytokines and their receptors to avoid destruction of the infected cell through apoptosis.

There are also a number of low molecular weight neuropeptides that display many of the same properties as cytokines but are not normally classified as cytokines or growth factors because of their size. Some of these low molecular weight proteins and peptides include Vasopressin, Bombesin from amphibians, Bradykinin and the Tachykinins. Many of these neuropeptides are pleiotropic and have dose and time dependent effects that provide a functional redundancy to cytokines.

The Tachykinins are a family of neuropeptides that were initially identified as neurotransmitters. Although they are not classified as cytokines, tachykinins also exhibit cytokine like activity. For example, tachykinins can activate neutrophilic granulocytes and stimulate the proliferation of T-cells. Tachykinins may also be involved in the release of cytokines by macrophages and granulocytes such as Interleukin 1 (IL1), Interleukin 6 (IL6), and (TNF-alpha) (IFN-gamma). Tachykinins may also stimulate the secretion of immunoglobulins as well as be involved in the regulation of non-infection inflammatory responses.

The tachykinin family of neuropeptides includes Substance P (SP) SEQ. ID. NO. 3; Neurokinin A (NKA) SEQ. ID. NO. 4; Neurokinin B (NKB) SEQ. ID. NO. 5; Neuropeptide K (NPK) SEQ. ID. NO. 6 and Neuropeptide gamma (NPγ) SEQ. ID. NO. 7. Each member of the family has a conserved amino terminal sequence ( . . . Phe-X-Gly-Leu-Met-NH2) SEQ. ID. NO. 8. With the exception of NKB, all of the neuropeptides are encoded by the prepro-tachykinin-I gene (PPTI). The PPTII gene encodes Neurokinin B. The sequence of the tachykinin neuropeptides can be seen in Table 1.

Substance P was first identified in 1931 from brain and gut extracts that exhibited smooth muscle contractile properties. The amino acid sequence of Substance P was first identified in 1971. Subsequent studies of the pharmacological properties of SP, NKA and NKB led to the identification of three distinct neurokinin receptors with preferred ligands. Substance P preferentially binds to the $NK_1$ receptor. NKA and NKB preferentially bind the $NK_2$ and $NK_1$ receptors respectively. However, each type of neurokinin is not highly selective and may bind to all receptor types with various affinities. In addition, these receptors may also bind Bombesin and similar peptides such as gastrin-releasing hormone under certain conditions.

The tachykinin receptors $NK_1$, $NK_2$ and $NK_3$ are from a group of transmembrane-spanning G protein-coupled receptors and have been associated with the activation of different second messenger systems within the cell. It is part of a system that converts external signals into intracellular messages. Generally, the receptors have a transmembrane domain that passes through the membrane seven times that has a highly conserved sequence. The amino terminal section of the receptor is positioned on the exterior of the cell and interacts with the ligand and the carboxyl terminal section is on the interior of the cell and is associated with one or more G-proteins. G-proteins typically have three subunits that can associate with a receptor, a target molecule and GDP or GTP. The G-protein can initiate cellular events directly or through a cascade of signaling events. For example, Substance P can stimulate phospholipase C and phospholipase A2 activity in different cell systems as a result of the activation of tachykinin receptors. Tachykinin receptor activation may also modulate calcium or sodium ion channel function in the cell.

It has been seen that Substance P (SP) and NKA are released from airway sensory nerves upon exposure to irritant chemicals and endogenous agents including bradykinins, prostoglandins, histamine, and protons. The released neuropeptides are potent inducers of a cascade of responses, including vasodilation, mucus secretion, plasma protein extravasation, leukocyte adhesion-activation, and bronchoconstriction. $NK_1$ receptors that are preferentially activated by SP are important for inflammatory actions, while $NK_2$ receptors that are preferentially activated by NKA mediate bronchoconstriction. Disease states such as inflammation or viral infections lead to enhanced peptide synthesis and an increased sensory nerve excitability. Together with increased $NK_1$ receptor synthesis and loss of major tachykinin-degrading enzymes such as neutral endopeptidase in airway inflammation, it has been suggested that recently developed, orally active nonpeptide neurokinin receptor antagonists could have a therapeutic potential in asthmatic patients. The released sensory neuropeptides are potent inducers of a cascade of responses collectively called neurogenic inflammation that have a similarity to several features of asthma.

Tachykinins also have been shown to increase vascular permeability in rat and guinea pig airways through the opening of endothelial gaps at postcapillary venules; SP is more active than NKA in this respect. Studies using receptor-selective synthetic agonists have suggested the involvement of $NK_1$ receptors for this effect. Tachykinins also potently increase airway blood flow, including trachea and nasal and bronchial mucosa, presumably via $NK_1$ receptors. Tachykinins exert bronchoconstrictor effects in most species, including man. NKA is more potent than SP in this respect. The $NK_2$ receptor mechanism has a revealed dominance for this response in human and guinea-pig bronchi. In the guinea pig, $NK_1$ receptors also mediate tachykinin contraction of bronchial smooth muscle, although it is less likely that tachykinins released from sensory nerves activate these receptors.

Substance P has also been shown to be a potent stimulator of airway mucus secretion in man and SP is a likely mediator of increased goblet cell discharge after exposure to cigarette smoke. By using selective agonists and antagonists the involvement of $NK_1$ receptors in tachykinin-induced mucus secretion from the airways has recently been defined. The potent secretagogue properties of SP on mucus have been confirmed in human nasal mucosa. Tachykinins also potentiate cholinergic neurotransmission in lower airways, mainly via $NK_1$ receptors. Tachykinins can modulate the function of a variety of inflammatory cells. Some of these reactions, e.g., mast cell and eosinophil granulocyte degranulation, are likely to be unrelated to the stimulation of specific neurokinin's and probably caused by direct stimulation of G proteins. There is no evidence that tachykinins degranulate lung mast cells in contrast to the situation in the skin. Substance P in very low concentrations may act as a mast cell primer to other agents when released from sensory nerves rather than as a direct degranulating agent. Alveolar macrophages are activated via $NK_2$ receptor stimulation. Furthermore, neutrophils are recruited upon sensory nerve activation in rat airways.

Tachykinins may also be involved in more long term effects, since both SP and NKA stimulate chemotaxis and proliferation of human lung fibroblasts, indicating a role in lung fibrosis. It is possible that both $NK_1$ and $NK_2$ receptors are involved in this response. Exposure to irritants causes sensory mechanisms to be upregulated. An increase in the responsiveness to tachykinins and an increase in the number of postcapillary venules contribute to the augmented plasma extravasation in these conditions. The number and length of SP-containing nerves in lower airways are increased in patients with fatal asthma. There is an increased expression of $NK_1$ receptors observed in the lungs of asthmatics and the reactivity to tachykinins is greater in allergic subjects both regarding bronchoconstriction and nasal congestion as well as wheal and erythema in the skin. (See Lundberg, Jan M. (1995) Tachykinins, sensory nerves, and asthma—an overview. Can. J. Physiol. Pharmacol. 73: 908-914).

Neurotransmitter receptors have also been shown to have the capacity to act as regulators of cellular proliferation, including airway smooth muscle (ASM) cells. Chronic asthma is characterized by ASM hyperplasia. SP induces a potent dose-dependent stimulation of ASM cell growth. However, NKA and NKB demonstrated little or no appreciable effect on airway smooth muscle cell proliferation.

These neuropeptides induce airway smooth muscle cell mitogenesis via transmembrane signaling mechanisms associated with specific activation of the $NK_1$ receptor. SP induced dose-dependent increases in ASM cell number within the concentration range of $10^{-14}$ to $10^{-4}$M. The maximum proliferative response was elicited with $10^{-4}$M. Neither NKA nor NKB induced significant proliferative responses in the ASM cells within the dose range of $10^{-12}$ to $10^{-6}$M, with the exception of NKA eliciting a relatively modest increase in ASM cell count at the highest administered concentration of $10^{-4}$M. Thus, tachykinin-induced ASM cell proliferation is mediated by selective activation of the $NK_1$ receptor.

Activation of the $NK_1$ receptor is also coupled to the activation of phospholipase A2 and phospholipase C via a PT-insensitive mechanism. Tachykinin-induced ASM cell growth was largely mediated by activation of NK1 receptors.

The pro-mitogenic effect of SP in cultured human skin fibroblasts is largely mediated by its interaction with the $NK_1$-receptor subtype. However, $NK_2$ and $NK_3$ receptor activation failed to show an inhibitory action on ASM cell growth. SP can elicit stimulation of phospholipase C and phospholipase A2 activity in different cell systems. ASM cells were found to be coupled to activation of phospholipase A2, the latter resulting in the release and pro-mitogenic autocrine action of certain eicosanoids, including thromboxane A2 and leukotriene D4. The pro-mitogenic action of SP is inhibited by selective blockade of the $NK_1$ receptor. The proliferative response to SP is near half-maximally blocked either by inhibition of phospholipase C or of phospholipase A2. (Noveral, James P., and Michael M. Grunstein. (1995) Tachykinin regulation of airway smooth muscle proliferation. *Am. J. Physiol.* 269 (*Lung Cell. Mol. Physiol.* 13): L339-L343).

Accordingly, there appears to be SP-induced regulation of airway smooth muscle cell growth and that the action of SP is mediated by transmembrane signaling events coupled to selective activation of the $NK_1$ receptor. The latter, together with recent evidence that $NK_1$ receptor gene expression may be enhanced in the lungs of asthmatic patients suggests a potentially important role for tachykinins, principally SP, in the pathogenesis of the airway smooth muscle remodeling found in asthma.

The neuropeptide Substance P was also found to stimulate DNA synthesis and cell growth for epithelial cells (cornea and lens) in a serum-free environment. Recently, it was also reported that SP stimulates release of PGE2 and proliferation in rheumatoid synoviocytes. These findings are in accord with other evidence that indirectly suggests that the release of tachykinins from sensory nerves in the skin, joints, and other peripheral tissues might function as mediators of local inflammatory and wound healing responses. In short term studies, (40 h) it was found that for lens and cornea epithelial cells, SP could stimulate DNA synthesis in a serum free environment; however, the lens cells were less responsive to SP unless insulin was present, while the cornea epithelial cells were sensitive to SP alone but showed little synergism in the presence of insulin. The results of pre-treating cells with SP, followed by the addition of either insulin or more SP, showed that addition of SP for a short time (2 h) can have an effect on the stimulation caused by subsequent addition of a second hormone. This would seem to indicate that either the dissociation rate for SP from its receptor is slow, or that the internal signals for DNA synthesis persist for quite some time.

Additionally, Substance P has been shown to activate malignant glial cells to induce cytokine release and proliferation, both responses being relevant for tumor progression. In various astrocytic/glial brain tumor-derived cell lines, the presence of tachykinin $NK_1$ receptor was seen to strictly correlate with the effect of SP or NKA of increasing DNA synthesis and cellular proliferation. In addition, SP may control many other glial responses such as taurine release, secretion of various cytokines (e.g. Interleukin IL-6, IL-8, transforming growth factor-β, leukemia inhibitory factor, granulocyte-macrophage colony stimulating factor) that are thought to be relevant for glioma progression. In fact, SP activates phospholipase C and stimulates the release of IL-6 and prostaglandin E2 from human fetal astrocytes in culture, and there is evidence for an up-regulation of this receptor by reactive proliferating astrocytes after transection of the optic nerve.

In addition, SP-immunoreactive astrocytes have been observed in multiple sclerosis plaques and in the forebrains of human infants. In fact, astrocytoma and glioblastoma cells contain significant levels of high affinity receptors for SP and their increase in expression correlate with the most malignant phenotype.

A human ovarian carcinoma cell line, lacking in tachykinin NK1 receptors and unresponsive to SP in terms of cell proliferation and DNA synthesis was used as a proof to assess the specificity of tachykinin NK1 receptor activation in glioma growth. These data suggest an involvement of tachykinins in supporting glioma progression. The presence of SP receptors in glioma cells is correlated with an increase in mitogenesis and cytokine release responsive to SP. The soluble factors (cytokines, prostaglandins, taurine) induced by SP activation in glioma cells are themselves tumor growth factors and can influence the tumor cell-host interactions including depression of the immune response, angiogenesis, and microenvironment modifications.

It has also been observed that the cells lining the mosquito larval gut as well as the saliva gland of the water strider display multiple chromosome copies e.g. endopolyploidy because something appears to inhibit the cell from dividing after the chromosomes have been replicated. The occurrence of endopolyploidy is believed to be the result of tachykinins present in the gut of mosquitoes as well as in the salivary glands of water striders. The saliva of the mosquito *Aedes aegypti* has been shown to contain a 1400-Da vasodilatory peptide with a sequence and pharmacological properties characteristic of a tachykinin. For example, the salivary peptide has been shown to have similar biological activity to mammalian tachykinins in endothelium-dependent relaxation of aortic ring studies and contraction of guinea pig ileum preparation studies as well as having cross desensitization with the vertebrate tachykinin substance P, and a positive reaction with anti-substance P antibodies.

The acquired mosquito vasodilator was purified to homogeneity and found to consist of two peptides: Sialokinin I SEQ. ID. NO. 1, with the sequence $Asn^1$-$Thr^2$-$Gly^3$-$Asp^4$-$Lys^5$-$Phe^6$-$Tyr^7$-$Gly^8$-$Leu^9$-$Met^{10}$-NH2, and Sialokinin II, SEQ. ID. NO. 2, identical to Sialokinin I except for the substitution of aspartic acid (Asp) for asparagine (Asn) in position 1. Sialokinin I (SK1) is typically present in amount of 0.62 μmol (711 ng) and Sialokinin II (SK2) is typically present in 0.16 μmol (178 ng) per salivary gland pair.

When assayed on the guinea pig ileum, both peptides had very similar potencies to that shown by substance P in a comparable assay, with K0.5 values of 6.58 nM for the Asn-derivative, 5.07 nM for the Asp-form, as compared to 4.94 nM for Substance P. There is some indication that the mosquito tachykinins produce stronger contractions at concentrations of $3 \times 10^{-8}$ M and above, but the physiological relevance of this is uncertain. (See Champagne, D. E. and J. M. C. Ribeiro (1994) Sialokinin I and II: Vasodilatory tachykinins from the yellow fever mosquito *Aedes aegypti. Proc. Natl. Acad. Sci.* 91, 138-142.)

Later, in a study of carboxyl-terminal heptapeptides having the sequence (I-II-Phe-III-Gly-Leu-Met-NH2), SEQ. ID. NO. 8, it was determined that two classes of tachykinins could be defined. The first class includes those peptides with Gln or Asn in position I and an aromatic amino acid in position III, related to substance P, and those with an aspartic acid (Asp) amino acid in position I and an aliphatic amino acid valine (Val) or isoleucine (Ile) in position III, related to Neurokinin A and Neurokinin B.

Substance P and related compounds interact with the $NK_1$ receptor, present in the guinea pig ileum among other tissues, and neurokinin-like peptides interact with $NK_2$ and $NK_3$ receptors, found for example in rat duodenum. It can be seen that the sialokinins mix characters of both tachykinin types, having an (Asp) amino acid at position I and a tyrosine (Tyr) amino acid at position III.

The model peptide results predict that the Sialokinins should be less active than substance P on the guinea pig ileum, but this was not observed to be the case. Although Munekata et al. concluded that the identity of the amino acid II was not important, the basic character of (Lys) in position II might compensate for the acidic (Asp) in position I, producing a more substance P-like carboxyl-terminal region with higher affinity for $NK_1$ receptors.

It can also be seen that tachykinins produce a variety of effects in addition to smooth muscle contraction and endothelium-dependent dilation. Substance P causes the release of histamine from mast cells and enhances human neutrophil phagocytosis, but these effects appear to be dependent on the sequence of basis of amino acids (Arg-Pro-Lys-Pro), SEQ. ID. NO. 9, at the carboxyl-terminal end and require micromolar concentrations in vitro or 100 nM concentrations in vivo. Some tachykinins that lack this sequence may inhibit the effect, because the carboxyl-terminal sequence is also involved in binding to a receptor on mast cells. On the other hand, substance P and neurokinins can activate macrophages at low concentrations, concentrations comparable to those required for smooth muscle contraction.

BRIEF SUMMARY OF THE INVENTION

One aspect of the invention is a system for providing a therapeutic dose of bioactive agent for use in treating a patient, and provides a volume of material that includes a tachykinin, or an analog or derivative thereof, stored within a container in substantially sterile form; and In one mode, the tachykinin or analog or derivative thereof comprises a sialokinin or an analog or derivative thereof. In a further embodiment, the sialokinin or analog or derivative thereof comprises SK1 or an analog or derivative thereof.

In another mode, the material includes a combination of SK1, SEQ. ID. NO. 1 and SK2, SEQ. ID. NO. 2 sialokinins or analogs or derivatives thereof. According to one further embodiment of this mode, the ratio of SK1 to SK2 sialokinins in the combination material is equal to about 4:1.

In another mode, the material further includes a carrier vehicle together with the tachykinin, and the tachykinin has between about 1 and about 10 nanomolar concentration in the carrier vehicle.

According to another mode, the material includes a carrier vehicle that is a non-sialokinin protein together with the tachykinin.

In still further modes, the tachykinin used may be naturally occurring, or in other modes may be synthesized.

In still another mode of this aspect, the container is provided as a vial with a needle puncture valve adapted to allow needle filling of the vial contents.

Another aspect of the invention is a system for treating an abnormal cellular condition at a location within a body of a patient, and includes a delivery catheter in combination with a volume of material that includes a tachykinin or an analog or derivative thereof. The delivery catheter has a proximal end portion, a distal end portion, and a delivery passageway extending between a proximal port along the proximal end portion and a distal port along the distal end portion. The volume of material is located within the delivery passageway such that the delivery catheter is adapted to deliver the volume of tachykinin or analog or derivative thereof at least in part to the location.

In one mode of this aspect, the delivery catheter comprises a guiding catheter, which in a further highly beneficial embodiment is a coronary guiding catheter.

In another mode of this aspect, the system further includes an implant and the volume of material is coupled to the implant. The implant is located within the delivery catheter, and the delivery catheter is adapted to deliver the implant with the volume of material at least in part to the location.

In a further embodiment, the implant comprises an endolumenal stent assembly, which in still a further embodiment includes a stent strut assembly and a coating on the stent strut assembly, whereas the volume of material is located within the coating.

In another embodiment, the endolumenal stent assembly is adapted to elute the volume of material into surrounding tissue over a prolonged period of time.

In still another embodiment, the endolumenal stent assembly comprises an endovascular stent assembly.

According to a further highly beneficial mode of this aspect, the tachykinin or analog or derivative thereof comprises a sialokinin or an analog or derivative thereof.

In one embodiment of this mode, the sialokinin or analog or derivative thereof is SK1 or an analog or derivative thereof.

In another mode of this aspect, the material comprises a combination of SK1 and SK2 sialokinins or analogs or derivatives thereof. The ratio of SK1 to SK2 sialokinins in the material according to one beneficial embodiment is equal to about 4:1.

In another mode, the material includes a carrier vehicle together with the tachykinin, and the tachykinin has between about 1 and about 10 nanomolar concentration in the carrier vehicle. In another mode, the material includes a carrier vehicle that is a non-sialokinin protein together with the tachykinin.

According to further modes of this aspect, the tachykinin or analog or derivative thereof is naturally occurring, or alternatively may be synthesized.

Another aspect of the invention is a method for treating an abnormal cellular proliferation condition associated with a region of tissue in a living patient, and includes the following steps: delivering a therapeutic dose of a material to the region of tissue; inhibiting the abnormal cellular proliferation condition with the therapeutic dose of the material; and furthermore wherein the material is a tachykinin or an analog or derivative thereof.

One mode of this aspect further includes diagnosing the region of tissue as having the abnormal cellular proliferation condition.

According to another mode wherein the region of tissue comprises a tumor, and the abnormal cellular proliferation condition comprises cancer, the method further includes: delivering the therapeutic dose of the material to the tumor; and inhibiting proliferation of the cancer with the therapeutic dose of the material.

According to another mode wherein the region of tissue comprises a wart, the method further includes: delivering the therapeutic dose of the material to the wart; and inhibiting growth of the wart with the therapeutic dose of the material.

In another highly beneficial mode according to this method, the tachykinin being delivered comprises a sialokinin or an analog or derivative thereof.

The sialokinin beneficially may be SK1 or an analog or derivative thereof. Moreover, the material may include a combination of SK1 and SK2 sialokinins. In this latter case, in a further embodiment the ratio of SK1 and SK2 in the material is equal to about 4:1.

According to still further modes, the sialokinin may be isolated from a natural source, or may be synthesized, as respective additional steps.

In still a further mode, the therapeutic dose being delivered according to this method comprises between about 1 to about 10 nanomolar preparation of the tachykinin. In a still further mode, the therapeutic dose comprises between about 0.5 to about 1 nanogram of tachykinin per millimeter of tissue being treated.

According to another mode, the therapeutic dose protocol includes delivering multiple bolus volumes of the material with a frequency over a duration that comprises a period of time for treatment, wherein the inhibition is achieved during the period of time.

In one embodiment of this mode, the multiple bolus volumes are delivered locally into the region of tissue. According to one further variation, the local delivery is performed via needle injection directly into the region of tissue.

In another embodiment of this mode, the bolus volumes are delivered via systemic delivery.

In still another embodiment, the duration is more than one day, and according to one further variation of this embodiment the frequency of bolus volume delivery is less than once daily.

In another embodiment, the multiple bolus volumes are substantially equivalent.

According to still another embodiment related to more extended treatments, the duration is at least about a two week period, and the therapeutic dose is generally between about 1 to about 7 nanograms of the tachykinin per milligram of the tissue being treated over the two week period.

In a yet further embodiment, the therapeutic dose protocol includes a daily average dose of that is between about 0.25 to about 0.5 nanogram of tachykinin per milligram tissue being treated per day over the duration. In a further variation of this embodiment, the multiple bolus volumes are not delivered every day over the duration.

According to another mode of the present aspect, the method further includes delivering the therapeutic dose into a body space wall within the body, which in a further embodiment involves delivering the therapeutic dose into a lumenal wall of a lumen within the body. In certain beneficial further variations, the region of tissue is located along the lumenal wall, and in one particular such variation, the therapeutic dose delivery into the lumenal wall includes delivering the therapeutic dose to a blood vessel wall. Further to this variation, the abnormal cellular proliferation condition inhibition further comprises inhibiting vascular smooth muscle cell proliferation. In yet another variation, the method further includes locally delivering the therapeutic dose to the vessel wall, such as by injecting the therapeutic dose locally into the vessel wall using a local needle injection catheter, such as of a type coupled to an expandable balloon.

According to another mode, the method eluting the material from an implanted endolumenal stent located at a region along the lumen associated with the region of tissue being treated.

According to yet another mode of this aspect, the method further includes injuring the region of tissue, and delivering the material to the region of tissue after the injury.

Another aspect of the invention is a method for providing a therapeutic preparation of bioactive agent to treat an abnormal cellular proliferation condition in a region of tissue associated with a body of a patient. The method according to this aspect includes the following steps: choosing a therapeutic dose of material based upon a known size of the region of tissue; coupling the therapeutic dose of material to a delivery system that is adapted to deliver the therapeutic dose to the region of tissue; and further wherein the material is a tachykinin or an analog or derivative thereof.

In one mode of this aspect, the therapeutic dose is coupled to a needle injector, and in another mode is coupled to an injection catheter.

In another mode, the tachykinin is a sialokinin or an analog or derivative thereof. In one further embodiment of this mode, the sialokinin is of the SK1 type. Moreover, the material may include a combination of SK1 and SK2, and in further variations of this embodiment the relative amounts of SK1 and SK2 present in the material is equal to about a 4:1 ratio, respectively.

According to still further modes, the sialokinin may be either isolated from a natural source or bioengineered source, or may be synthesized.

Another mode of this method further includes preparing the therapeutic dose by combining a first tachykinin material with a second material.

In another mode, the therapeutic dose is chosen based upon a measured volume of the region of tissue to be treated. In one particular beneficial embodiment for treating a wart, the therapeutic dose is chosen based upon a measured size of the wart. In another embodiment for treating cancer, the therapeutic dose is chosen based upon a measured size of the cancer tumor.

Another aspect of the invention is a method for treating a wart by delivering a therapeutic dose of material comprising tachykinin or an analog or derivative thereof to the wart.

According to one highly beneficial mode of this aspect, the tachykinin or analog or derivative thereof being used is a sialokinin or analog or derivative thereof, which may include SK1 or an analog or derivative thereof in one example, or a combination of SK1 and SK2 tachykinins or respective analogs or derivatives thereof in other embodiments, such as according to a ratio between SK1 and SK2 of about 4:1 in still further variations.

The sialokinins according to this aspect may be isolated from a naturally occurring or bioengineered source, or may be synthesized.

Another aspect of the invention is a method for treating a tumor by delivering a therapeutic dose of material that includes tachykinin or an analog or derivative thereof to the tumor.

In one highly beneficial mode of this aspect, the tachykinin or analog or derivative thereof comprises a sialokinin or an analog or derivative thereof, which may according to one example be SK1 or an analog or derivative thereof, or in another example may include a combination of SK1 and SK2 tachykinins or analogs or derivatives thereof. In one further variation of the latter embodiment, the ratio of SK1 to SK2 present in the material is equal to about 4:1.

The sialokinin according to this aspect may be either isolated from a naturally or bioengineered source, or may be synthesized.

Another aspect of the invention is a method for providing a pharmacological preparation of sialokinins or analogs or derivatives thereof, and includes synthesizing at least one of SK1 and SK2 or an analog or derivative thereof in substantially pure form.

One mode of this aspect further includes synthesizing both of SK1 and SK2 or their analogs or derivatives thereof, and providing the synthesized SK1 and SK2 or their respective analogs or derivatives thereof in a combination material. According to one embodiment of this mode, the method further includes providing the SK1 and SK2 in about a 4:1 ration in the combination material, respectively. In another embodiment, the method includes providing the combination material in a substantial powder form. Further to this latter embodiment, in one variation the method may further include mixing the powder with a carrier vehicle to provide an injectable material.

In another mode of this aspect, the method further includes sterilizing the synthesized sialokinin.

Another aspect of the invention is an endolumenal stent with a stent body that includes a bioactive tachykinin material. The stent is adapted to elute the tachykinin into a lumen wall engaged therewith when placed in-vivo. In one particular beneficial mode, the stent is a vascular stent, and further beneficially is a coronary stent. According to one further mode, the stent body includes a stent strut system with a coating thereover that stores and elutes the tachykinin material. In another mode, the stent struts of an interconnected network of struts include reservoirs that store the material. In still another mode, a cover material such as a polymeric graft stores and elutes the tachykinin. The tachykinin is provided as a particular type and at sufficient therapeutic dose to substantially effect at least one of: vasodilation, smooth muscle cell proliferation, smooth muscle cell migration, and restenosis. In particularly beneficial modes, the tachykinin is a sialokinin.

According to further highly beneficial modes of the various aspects above, sialokinin is used of a similar structure and bioactivity as that taken from *Aedes aegypti* mosquito saliva having specifically beneficial observed bioactivities according to mechanisms considered well suited for the intended purposes of the invention.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only:

FIG. 5 shows a transverse cross-section through a strut of one type of Sialokinin eluting stent according to another aspect of the invention.

FIG. 6 shows a transverse cross-section through a strut of another type of Sialokinin eluting stent according to another aspect of the invention.

FIG. 7 shows a transverse cross-section through a strut of still another type of Sialokinin eluting stent according to another aspect of the invention.

FIG. 8 shows a transverse cross-section through still another type of Sialokinin eluting stent according to another aspect of the invention.

DETAILED DESCRIPTION OF THE INVENTION

Figure 1:
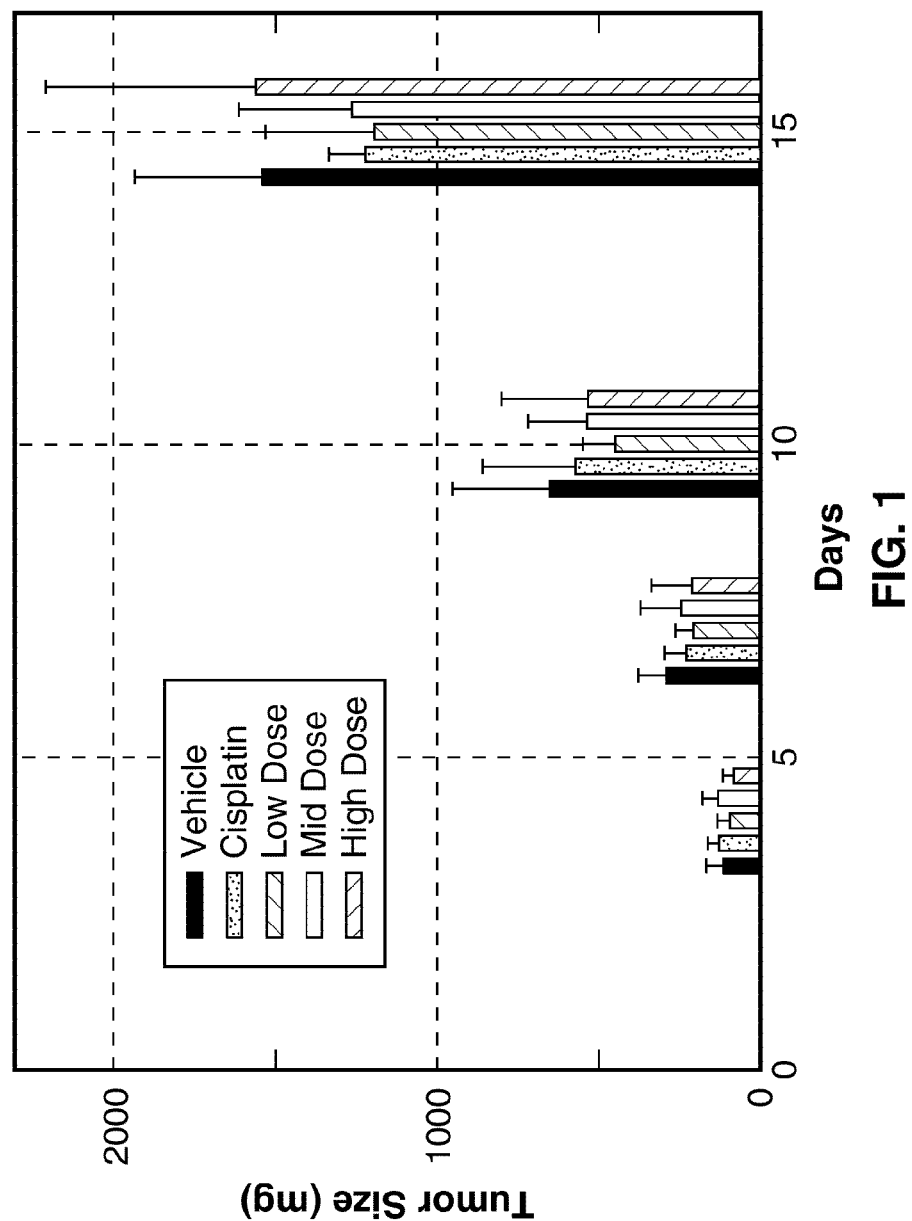
FIG. 1 is a graph depicting in vivo dosing and toxicity results according to one aspect of the present invention.

Referring more specifically to the drawings, for illustrative purposes the present invention is embodied in the methods and apparatus generally shown in FIG. 1 through FIG. 8. It will be appreciated that the apparatus may vary as to configuration and as to details of the parts, and that the methods may vary as to the specific steps and sequence, without departing from the basic concepts as disclosed herein.

The present invention provides substantial advancement beyond past research and investigation studying the molecular biological activities of tachykinins in general, and Sialokinins in particular, and provides therapeutic applications of these compounds to generally hyperproliferative cellular conditions.

The present invention therefore involves the treatment of unregulated areas of cellular proliferation such as tumors, warts, sclerotic plaquing, fibrosis including the inhibition of arthritic fibrosis development in the joints, focal lesions, restenosis or sarcoma and the like in the mammalian body by administering specific tachykinins to those areas of unregulated cellular proliferation.

More specifically, Sialokinins SEQ. ID. NO. 1 and NO. 2 are prepared for either local or systemic delivery for therapy to hyperproliferative tissue structures as follows. The tachykinin itself is generally synthesized as described in finer detail herein, but may also be either isolated from naturally occurring sources (e.g. mosquitoes or their endogenous cells producing the sialokinins), or may be produced by bioengineered cell cultures in the laboratory, to suit particular commercial needs. Once so prepared, it is prepared in solution with an appropriate carrier vehicle for injection or systemic delivery modalities, or provided in a device coating as also elsewhere herein described. It may be further sterilized prior to delivery, and thus may be either injected directly into the tissue structure to be treated, or delivered systemically, or provided with an implant coating for elution delivery, depending upon the particular therapy to be employed.

In general, the preparation of sialokinin for therapeutic use according to the various detailed embodiments described in the Examples incorporates a combination of SK1 and SK2 in a 4:1 ratio. This is generally based upon prior published research identifying this ratio in the natural occurrence with the *Aedes aegypti* mosquito. Moreover, this ratio has been shown efficacious and safe in the various experimental examples shown below. However, there is some debate about the actual presence of SK2 in nature, and whether or not its occurrence is an anomaly of isolation. Nevertheless, the SK2 conformation has been studied and characterized as exhibiting various bioactive properties that are similar to SK1, including preferential competition with Substance P, though to a lesser extent than SK1. Accordingly, where the SK1/SK2 combination is herein described and used in the present embodiments, substitute preparations of SK1 alone is likely to be more active in certain aspects. Accordingly, the various references in the embodiments herein to naturally occurring compounds of Sialokinins are intended to apply to both SK1 alone, as well as combinations of SK1 & SK2, either in the 4:1 ratio or otherwise. Moreover, functional or structural equivalents are also contemplated, such as in particular compounds incorporating similar active sites and related bioactivities as described herein. Moreover, other variations are contemplated, including for example "pro-drug" preparations providing a compound that is delivered into the body and thereafter modified to release a Sialokinin or analog or derivative thereof, such as by enzymatic cleaving or other form of metabolism or chemical or biological action.

It is to be further appreciated according to certain further embodiments that therapeutic preparations of Sialokinins and related methods include identifying, and in some cases preparing, a particular therapeutic dose to meet a particular proliferation condition in tissue, more specifically based upon the extent of need, and most typically based upon size (e.g. volume or area) of tissue to be treated. For example, in the case of tumors or warts as described herein, a particular dose is identified in relation to the size of the tumor or wart structure. While the particular experimental examples of course provide particular dose/tissue volume correlations, others may be readily identified to meet a particular need, such as for example applying a "per milligram" tissue multiplier to the size of the structure, though such dosing calculation will typically be limited to particular ranges of overall drug delivery in this regulated field, and moreover the ratio correlation may not prove to be linear for all circumstances.

It is also to be appreciated that the terms "dose" or "dosing" are herein intended to include both a definition related to quantity, concentration, volume, and/or rate of delivery in the acute administration setting, as well as a temporal definition that includes frequency and duration of a multiple treatment protocol to provide an overall therapeutic effect. The various experimental examples provided herein provide highly beneficial insight into both local injection and systemic (for tumors) dosing regimes to treat cancer and warts, respectively. However, it is to be appreciated that such may be modified to suit a particular need. For example, a series of acute administrations of 0.5 to 1 µg/mg tissue every other day for 15 days may be replaced with halved acute dosing every day (or twice the frequency). Or, the acute dose may be increased to larger bolus deliveries, e.g. 3/2 times the dose but delivered every third day rather than every other day. As well known in the art, however, such modifications to chronic dosing of pharmaceuticals often does not result in the same outcomes, and at certain outer limits efficacy, safety, or both may be compromised (e.g. a single 15 mg/ml bolus dose may not be tolerated well and may not have 30 day long efficacy such that it is not a suitable substitute form of therapy to the 1 µg/mg tissue dose every other day for that period).

It is also to be appreciated that the particular embodiments provided in the experimental examples, while illustrative of broader beneficial aspects of the invention, are also themselves highly beneficial. For example, it has been determined that dosing between 1 to 10 µMolar is a beneficial range, but that the range of 5 to 10 µMolar is in particular beneficial, and in particular 5 µMolar is considered beneficial in many circumstances.

Accordingly, among the various embodiments it is to be appreciated that the therapeutic preparation of tachykinin to a therapeutic dose based upon a diagnosed cellular proliferation condition is considered a broadly beneficial aspect of the invention, and in particular as applied to sialokinins.

The invention may be better understood with reference to the accompanying examples, which are intended for purposes of illustration only and should not be construed as in any sense as limiting the scope of the present invention as defined in the claims appended hereto.

Example 1

Biologically active peptides of approximately ten amino acids in length of the present invention are preferably synthesized in vitro. The preferred sequences are SEQ. ID. NO. #1 for Sialokinin I (SK1) with the sequence $Asn^1$-$Thr^2$-$Gly^3$-$Asp^4$-$Lys^5$-$Phe^6$-$Tyr^7$-$Gly^8$-$Leu^9$-$Met^{10}$-NH2, and for SEQ. ID. NO. #2 for Sialokinin II (SK2) with the $Asp^1$-$Thr^2$-$Gly^3$-$Asp^4$-$Lys^5$-$Phe^6$-$Tyr^7$-$Gly^8$-$Leu^9$-$Met^{10}$-NH2. The superscripts denote the position of the amino acid from the carboxyl terminal end.

This preferred sequence represents many different beneficial bioactive aspects observed for sialokinins. Moreover, many such aspects of the sialokinin bioactivity have been isolated to particular sites along the sequence. In particular, the sequence(s) representing amino acid chains at sites 5 through 10 in many cases, or sites 3 through 10 in other cases, have been observed to provide the active site for bioactivity. Accordingly, analogs or derivatives of sialokinins considered suitable for use according to many of the embodiments would include for example modified peptide structures which nevertheless provide these sequences in similar biologically active form. Other conservatively modified variants are further contemplated as would be apparent to one of ordinary skill based upon the totality of this disclosure together with other available relevant information.

One preferred method of synthesis generally has the following steps:

1. Measure out the appropriate quantity (adjusted to match desired quantity of completed peptide) of HMP (Wang) resin fluoren-9-ylmethoxycarbonyl (Fmoc) amino acid (AA) for position 1. Use Wang resin Fmoc Asn to synthesize Sialokinin I or Wang resin Fmoc Asp to synthesize Sialokinin II. Other resins are available and would make suitable replacements for Wang resin and any resin with 4-hydroxymethylphenoxy substitution, etc. could be used in the alternative. For example, the synthesis process can also be conducted with BOC rather than Fmoc protected α-amino acids. BOC synthesis requires the addition of hydrogen fluoride (HF) during the deprotection step to deprotect the side groups. 2-(4-biphenyl)propyl [2]oxycarbonyl (Bpoc) or 6-nitroveratyl-oxycarbonyl (Nvoc) etc. are also viable options for α-amino acid protection. Although it involves an extra step, unacylated resins can also be used but the position 1 amino acid must be linked to the resin before the repetitive acylation can begin.

2. Wash resin and first amino acid with 10 ml dimethylformamide (DMF) for 1 min. Drain. The wash is preferably repeated three times.

3. In order to deprotect the α-amino acid, 20% piperiden/DMF for 20 minutes is added and later drained.

4. Wash with 10 ml DMF for 1 min. Drain. The washing is preferably repeated three times to remove piperiden from the resin and growing amino acid chain.

5. The subsequent amino acid from the predetermined sequence is added as the next link in the amino acid chain by reacting 1/3 Fmoc AA (selected for position 2-10), 1/3 1-hydroxybenzotriazole (HOBt), and 1/3 1,3-diisopropylcarbodiimide (DIC) for 1 hour. Drain. It will be seen that various other activating agents such as benzotriazole-1-yloxy-trisphoshonium hexafluorophosphate (PyBOP) and auxiliary nucleophiles such as N-hydroxy-5-norbene-endo-2,3-dicarboxamide (HONB) can be also be used for the acylation process.

6. Uncoupled amino acids and other reactants are then removed with a wash of 10 ml DMF for 1 min. The wash is drained and preferably repeated three times.

7. The amino acid of the amino terminal end of the growing peptide is deprotected with 20% piperiden/DMF for 20 minutes and drained.

8. Removal of the piperiden is accomplished with a wash of 10 ml DMF for 1 min and then drained. The wash is preferably repeated three times.

9. This sequence of steps 5-7 is repeated for each consecutive amino acid in the desired peptide. Alternatively, the synthesis process can be conducted under continuous flow rather than the batchwise sequence and thereby avoid the manual wash and drain repetitions. When the peptide is complete, a mixture of 5% H2O/5% ethanedithiol (EDT)/90% trifluoroacetic acid (TFA) is added to the final product for approximately 2 hours. A 10:1 solution to reagent ratio is preferred. TFA is used to cleave the peptide from the resin and deprotect the amino acid side chains. The H2O and EDT serve as scavengers. In addition, other compounds such as anisole, thioanisole and ethylmethyl sulphide may be used in excess to serve as scavengers to avoid formation of cationic species that tend to alkylate the reaction components.

The results of the synthesis are preferably precipitated in 10% by volume cold ether and the precipitate filtered or centrifuged. The peptides are then preferably dissolved in 90% acetic acid, lyophilized and purified by reverse phase column high-pressure liquid chromatography (HPLC) with C18 column. Purification can also be accomplished with gel filtration, ion exchange, and reversed-phase and ion exchange high performance liquid chromatography (hplc) either individually or in combination for achieving the desired level of peptide purity.

Example 2

The inhibitory action of Sialokinin I and II, SEQ. ID. NO. 1 and NO. 2, against tumor tissue proliferation (Lewis lung carcinoma) was investigated. To test the efficacy of three different concentrations of peptide test articles in an in vivo tumorigenicity model using Lewis lung carcinoma cells.

Lewis lung carcinoma cells were obtained from ATCC and cultured in monolayers in DMEM supplemented with 10% heat-inactivated FBS, 4 mM L-glutamine, 100 µg/ml streptomycin and 100 units/ml penicillin for two passage cycles at 37° C. in 95% air and 5% $CO_2$. Cells were harvested from subconfluent cultures by 60-second exposure to trypsin/EDTA, washed in serum free medium and brought to the correct concentration of cells in PBS.

On day 0, 35 female C57Bl/6 mice 6-8 weeks of age were shaved on the right lateral thorax and injected subcutaneously with $1.0 \times 10^6$ Lewis lung carcinoma cells. A total of 35 mice were injected so that 25 tumor-bearing mice with the correct tumor size could be used for the study. Tumors were allowed to develop for four days post cell injection at which time biweekly tumor measurements (L×W), in millimeters, were recorded for 3 weeks. These data were converted to weight (mg) using the following formula: mg=$(L \times W^2)/2$. The data are presented as mean tumor mass plotted over time.

When tumors reached a size of 100-200 mg, 25 mice were selected and randomly sorted into five groups. The five groups of Lewis lung tumor bearing mice were used to test three different test article concentrations.

The first group contained animals injected with the test article carrier as a control group. The control animals were injected with 50 µl intra-tumor injections of sterile saline and 1% bovine serum albumin (BSA), three times per week for a total of 5 doses. The control group contained mice that received the vehicle as a negative control.

The second group contained animals treated with 6 mg/kg of Cisplatin (Platinol; Bristol-Myers Squibb Co.) as a positive control administered according to manufacture's specifications by intravenous tail vein injection, every fourth day for a total of 3 doses. The Cisplatin group contained mice that received Cisplatin as a positive control.

The third group contained animals that received 5 µM of test article dissolved in sterile saline and 1% bovine serum albumin (BSA) injected intra-tumor with 50 µl injections, three times per week for a total of 5 doses.

The fourth group contained animals that received 10 µM of test article dissolved in sterile saline and 1% bovine serum albumin (BSA) injected intra-tumor with 50 µl injections, three times per week for a total of 5 doses.

The fifth group contained animals that received 100 µM of test article dissolved in sterile saline and 1% bovine serum albumin (BSA) injected intra-tumor with 50 µl injections, three times per week for a total of 5 doses.

Injections began on the day that animals were randomly sorted into one of five groups. Animals in the control, 5 µM, 10 µM, and 100 µM groups were dosed every other workday with an intra-tumor subcutaneous injection for a total of 5 doses. Tumor size was measured and recorded twice weekly using calipers. Mice were examined twice weekly for morbidity, and any abnormal findings were recorded. When tumors reached a mean target size of 1000 mg in control mice the animals were euthanized and two mice from each group were randomly selected and sent to necropsy for tumor and tissue collection. Mice were photographed before harvesting tumors and major organs (heart, lung, liver, kidney, spleen, GI tract and brain). No mice died while on study.

There was also an absence of measurable toxicity in Lewis lung carcinoma trial. Comparing animal body weight measurements taken at the beginning and end of the trial, there was no measured detectable toxicity. (Weight loss during treatment is a recognized indication of toxicity.) Necropsy of the trial animals failed to reveal detectable macroscopic or microscopic evidence of test article-related toxicity. Of note, the animals given Cisplatin experienced significant weight loss.

Figure 2:
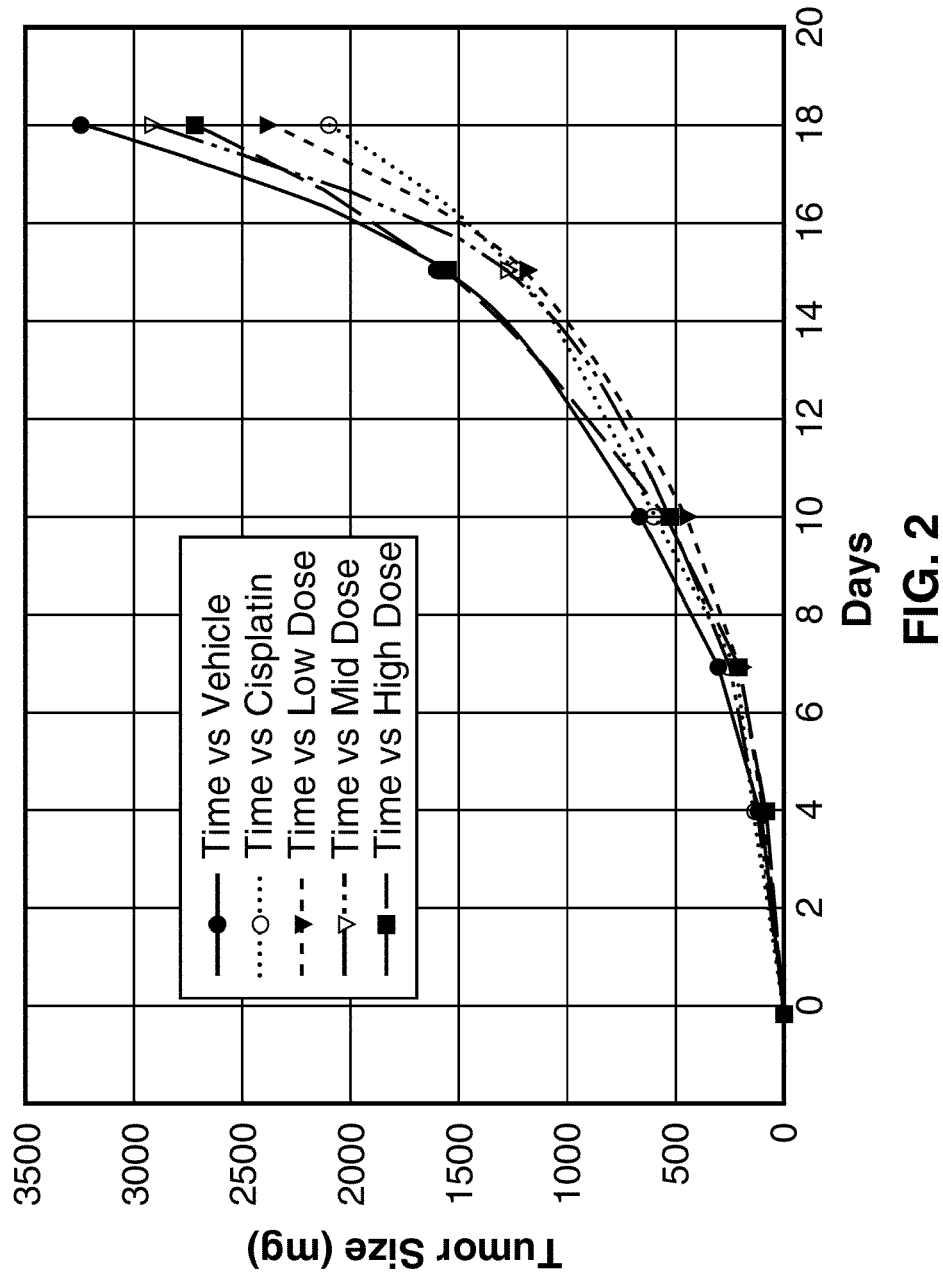
FIG. 2 is a graph of tumor growth over time at different dose levels of Sialokinins according to one aspect of the invention.

Referring now to FIG. 1 and FIG. 2, comparisons of the tumor growth of control group with the 5 µM and 10 µM test article groups can be seen. An inhibitory action against tumor tissue proliferation was observed in the 5 µM and 10 µM test article groups. As expected vehicle treated, control, mice developed the largest tumors while mice treated with Cisplatin developed significantly smaller tumors ($p<0.05$). In addition, mice that received 5 µM of test article developed significantly smaller tumors ($p<0.05$) when compared to control group mice. This represents a 36.4% inhibition of tumor growth.

Overall, the 5 µM group showed 63, 64, and 84% growth compared to the control tumor growth on day 7, 10, and 15, respectively. The 10 µM group showed 62, 80, and 82% growth compared to control tumor growth on day 7, 10, and 15, respectively. For reference, the Cisplatin treated group showed 58, 93, and 73% growth compared to control tumor growth on day 7, 10, and 15, respectively. The 100 µM group, which was intended mainly for toxicity information, showed little beneficial action as the trial progressed.

Example 3

To test the efficacy of different concentrations of the Sialokinin peptides, test articles, SEQ. ID. NO. 1 and NO. 2, in an in vivo tumorigenicity model, a study was conducted with Lewis lung carcinoma in immuno-compromised (nu/nu) mice. Lewis lung carcinoma cells were cultured in Dulbecco's Modified Eagles Medium (DMEM), supplemented with 4 mM L-glutamine, 0.1 mM non-essential amino acids, 10% heat inactivated fetal bovine serum (FBS), 50 mg/ml Gentamicin and 250 µg/ml Fungizone. Cells were cultured in 5% $CO_2$ and 95% air at 37° C. Exponentially growing cells were harvested and washed twice in phosphate buffered saline (PBS) to remove any traces of trypsin or serum. The washed cells were suspended in Hanks Balanced Salt Solution (HBSS) for injection.

Athymic nude mice were injected subcutaneously in the right lateral thorax with $10^4$ Lewis lung carcinoma cells. A total of 38 mice were injected, with 33 tumor-bearing mice used in the study. When tumors reached a target window size of 100-200 mg, 33 tumor-bearing mice were randomly selected and sorted into one of three groups. Group 1 contained mice that received the test article carrier by an IV injection as a negative control. Groups 2 and 3 contain mice that receive 5 μM or 10 μM test article doses. Test and control articles were administered by an intravenous (IV) tail vein injection three times per week for two weeks.

Tumor measurements were recorded three times a week using calipers. Group weights were taken prior to dosing and once weekly for the duration of the study. Clinical observations on each mouse were done twice weekly for signs of toxicity and morbidity and any abnormal findings were recorded. All mice were submitted for necropsy. The following tissues were collected: the heart, lung, liver, kidneys (2), spleen, GI tract (stomach, duodenum, jejunum, ileum, cecum, colon), brain (cerebrum, cerebellum), and site of tumor cell injection with mass.

Necropsy reports of the immuno-compromised mice which received 200 μl intravenous injection of 5 μM and 10 μM concentrations of the peptide showed no detectable toxicity or tissue necrosis. Because weight loss in study animals during or post dosing period is often considered a simple indication of toxicity, weight measurements were taken during the study period. No weight loss was detected in study group animals.

Figure 3:
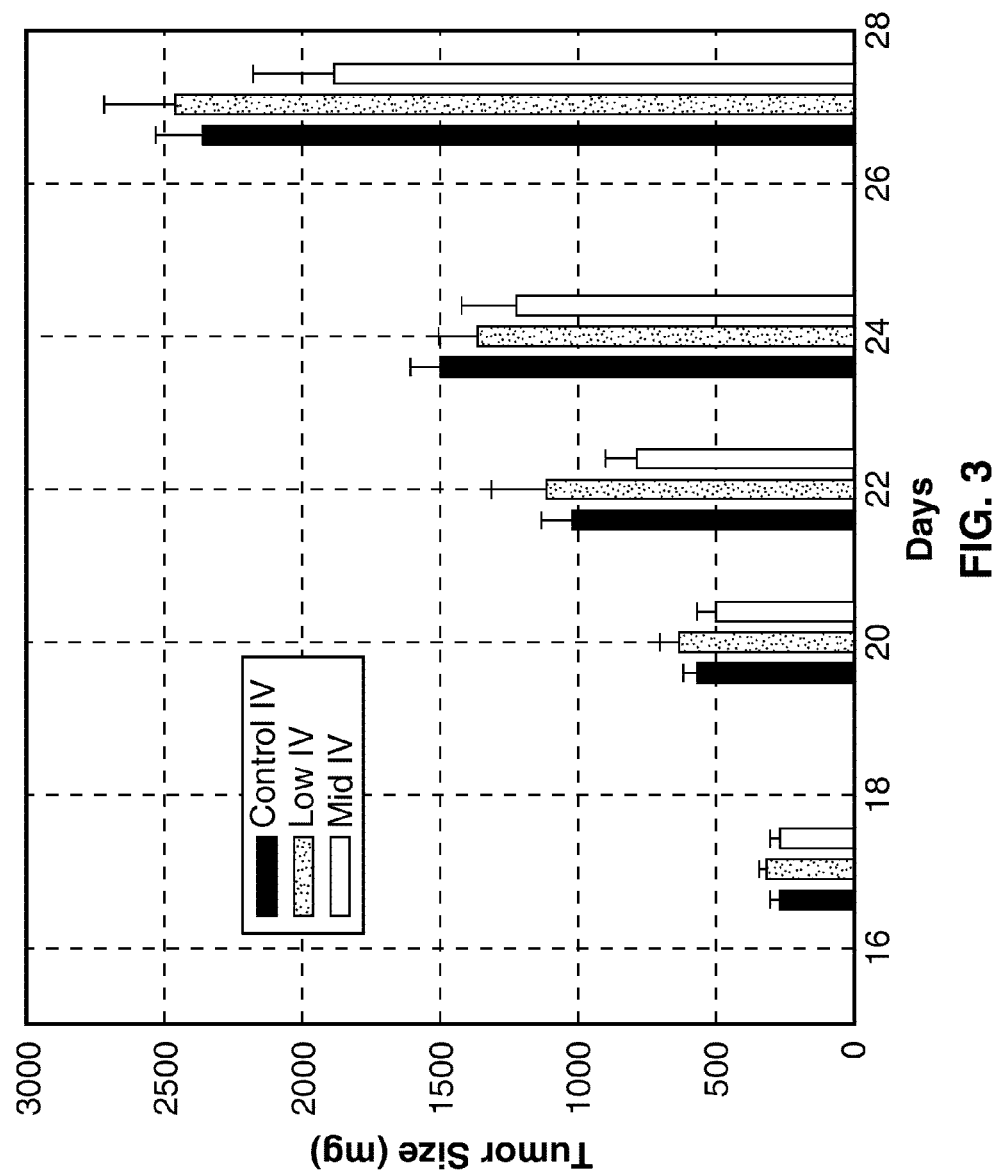
FIG. 3 is a graph of tumor growth over time at different dose levels of Sialokinins according to one aspect of the invention.
Figure 4A:
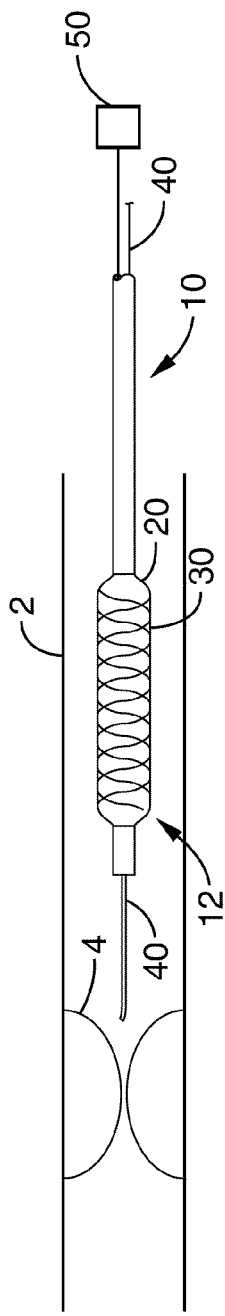
FIGS. 4A-C show various modes of using a drug eluting stent to treat an occluded region of a blood vessel according to a further aspect of the invention.
Figure 4B:
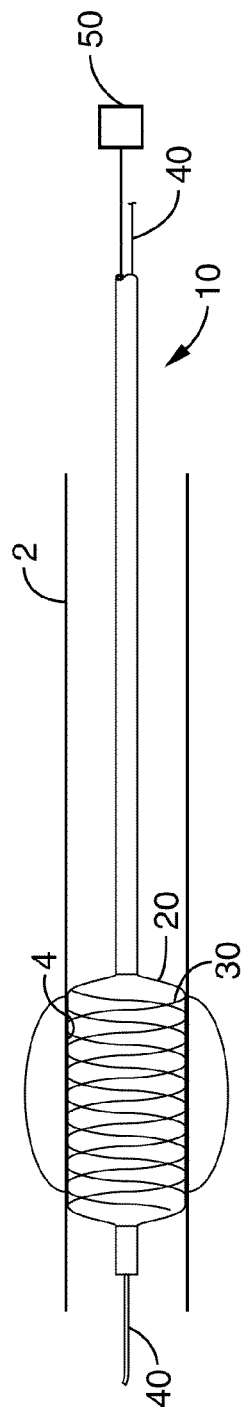
Figure 4C:
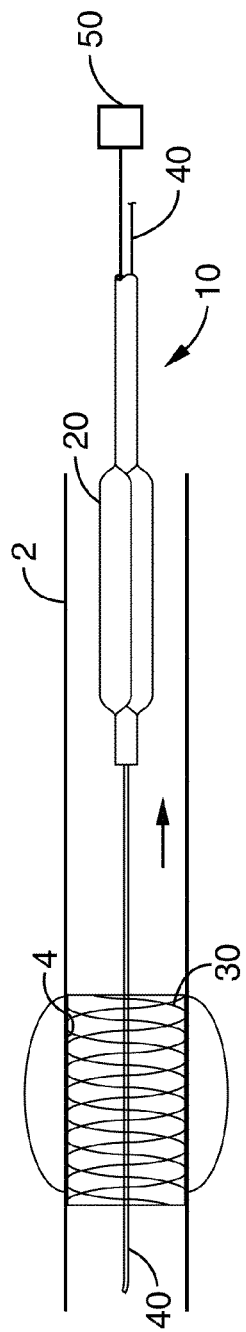

Turning now to FIG. 3, a graph of tumor size over time for mice that received 200 μl intravenous injections of 5 μM and 10 μM concentrations of the peptide is shown. The dosing of 5 μM and 10 μM concentrations of the peptide in the injection is equivalent to 0.05 mg/kg and 0.1 mg/kg, respectively. It can be seen that the intravenous injection showed inhibitory action at 10 μM concentrations (0.1 mg/kg). Tumor growth was inhibited by 20% throughout the study period. Although this data shows significant action, IV dosing at 50 μM concentrations (0.5 mg/kg) should show much greater benefit in tumor inhibition.

Example 4

Human papilloma virus (HPV) infection is an example of a viral disruption of the proliferative balance in cell cycle control. The human papilloma virus (HPV) is responsible for a variety of human epithelial diseases affecting the cutaneous and mucosal epithelia and causing papillomas (warts) and benign or malignant neoplasms. The HPV is a serious concern because about 10% of the population has warts of one form or another. This makes HPV an issue even from a strictly cosmetic point of view. The most serious concern is the genital carcinoma (especially cancer of the cervix), which is caused by HPV. "It is estimated that 500,000 new cases of cervical neoplasia are diagnosed per year (primarily squamous carcinomas). Thus, HPV-associated cancer represents one of the most common causes of cancers afflicting women and is one of the three most common causes of cancer death among women globally" (Saunders, N. A. and I. H. Frazer, (1998) Simplifying the molecular mechanisms of human papilloma virus. *Dermatol Clin.* 16, 823-827).

Human papilloma virus (HPV) infection typically begins by inoculation of an epithelial wound with the viral particles (Ragland et al., 1994). The HPV's double stranded DNA is taken in by a nearby cell and commandeers the host cell's transcriptional machinery to coordinate the expression of viral gene products in a specific spatiotemporal sequence within the differentiating epithelial layer. In this way the early genes are expressed in proliferating undifferentiated keratinocytes. The HPV proteins E5, E6, and E7, are responsible for HPV-associated tumor development. The E5 protein inactivates tumor suppressor gene p21 and stimulates human growth factor activity, enhancing cell proliferation and possibly influencing transformation to malignancy. Protein E6 binds to the tumor suppressor p53 gene targeting it for destruction, as well as binding to the p53 protein which has been referred to as the 'guardian of the genome' (Flaitz, C. M. and M. J. Hicks (1998) Molecular piracy: the viral link to carcinogenesis. *Oral Oncology.* 34, 448-453).

When activated by mutational stimuli, such as ultraviolet- or gamma-irradiation, p53 induces the expression of gene product p21, which inhibits the cell cycle until such time as any DNA damage is repaired. If the DNA damage is too great, then p53 induces apoptosis. Thus, the inactivation of p53 protein by E6 has a dual effect; it removes a proliferative brake from the cell and also leads to genomic instability and mutational inheritance (Saunders and Frazer, 1998). The E7 protein acts as a tumor-promoting agent by binding the tumor-suppressor genes pRb and p107. These tumor suppressors are negative regulators of the viral expression and proliferation-regulating factors, the E2 family. Thus, binding and inactivation of pRb, or p107 leads to the release of cells from negative growth signals and leads to unregulated growth control in the keratinocytes (Saunders and Frazer, 1998; Flaitz and Hicks, 1998). In instances of HPV-infection site transformation to malignancy, the viral DNA is integrated into the host DNA sequence. This integration often causes previously mentioned E2 gene (which regulates expression of viral genes and viral replication) to be disrupted (Hedge, R. S, and E. J. Androphy (1998) Crystal structure of the E2 DNA-binding domain from human papilloma virus type 16: Implications for its DNA binding-site selection mechanism. *J. Mol. Biol.* 284, 1479-1489), allowing the E5, E6, and E7 gene products to be produced in a completely deregulated fashion that leads to continued expansion of this malignant cell population. With the cellular controls by p53, p21, and p107 inactivated there is no mechanism to stop the uncontrolled differentiation.

A trial was conducted to observe the anti-proliferative action of Sialokinins, SEQ. ID. NO. 1 and NO. 2, in the treatment of warts in a human application. This trial, conducted by a dermatologist, involved four volunteer human subjects who received two (2) subcutaneous injections of Sialokinin I and Sialokinin II into the wart. Injections of 100 μl of 5 μM were administered subcutaneously to each volunteer.

The warts chosen for this trial had been diagnosed as stable and thus any observable change in the size of the wart to the injections would be significant. During the period of treatment with Sialokinin I and Sialokinin II, 3 of the 4 patients showed a reduction in wart size. Of the 3 patients, reductions in size of 19%, 79%, and 31% were observed. When no further treatments were administered, no further reductions were observed.

In a non-clinical observation, common Canadian brown mosquitoes of unknown species indigenous to Southern Canada were induced to bite papillomatous warts in a single patient. The warts were observed to disappear and normal epithelial growth to resume with no residual keratosis.

Accordingly, It can be seen that a therapeutically effective dosage from approximately 5 μM to approximately 10 μM of mosquito salivary tachykinins may be injected into unregulated mammalian tumor, wart tissue, or area of unregulated proliferation to induces the previously mentioned immunophysiologic mechanisms to control proliferation. Likewise, a therapeutic dosage from approximately 0.05 mg/kg to approximately 1 mg/kg body weight of mosquito salivary tachykinins can be provided systemically or applied topically to control proliferation.

Thus, mosquito salivary tachykinins appear to not only inhibit cellular division by acting on the NK-receptors and the immuno-physiologic mechanisms they modulate by stimulating some mechanisms and inhibiting others, but also cause the mammalian body to combat unregulated cellular proliferation through suppression or apoptosis. Vasodilation, increased vascular permeability in the area of injection, and inhibition of mast cell degranulation may also be observed.

The results of Example 2 through Example 4 suggest that the disappearance of the unregulated tissue by apoptosis of the cells in the tumor or wart may occur. In cases of HPV, stimulation of the host organism's immune system to attack viral protein E6, allows mammalian p53 and p21 to reassume control and the polyp will destroy itself by self-induced cell death. The regeneration of fibroblasts and properly regulated epithelial proliferation necessary for repair of the area disrupted by unregulated cellular proliferation are also expected. In the HPV example, host immune inactivation of viral E5 protein will allow tumor suppressor gene p21 to function and regulate growth factor activity, controlling cell proliferation and stopping possible transformation to malignancy. Host immune attack on HPV E7 protein expression will enable the affected cells to resume tumor suppression through actions of pRb and p107. Once the unregulated proliferation has been suppressed, mosquito salivary tachykinins may also regulate epithelial proliferation in areas of epithelial damage inducing healing of the tumor-damaged area. Thus, Sialokinins offer a minimally intrusive and nearly painless treatment. The use of invertebrate mosquito salivary tachykinins may also be used instead of a receptor antagonist in mammals will function to bind to the mammalian tachykinin receptor cites because of their chemical similarity to mammalian tachykinins TKA, TKB, and SP and carry with them the powerful physiological and immune system stimulating abilities of the mosquito tachykinin on the mammalian body. Thus the use of mosquito salivary tachykinins on mammalian tumors will, in some cases, actually stimulate the mammalian body to destroy the tumor rather than simply inhibit its growth as in the case of the previously mentioned $NK_1$ receptor antagonist.

Cancer is just one of many applications of Sialokinins. Other applications may include such illnesses as multiple sclerotic plaquing, arterial restenosis and plaquing, asthma (prevent inflammatory response in mild asthma and fibrosis in more severe cases), warts (stop proliferation and prime the body to destroy the unregulated cellular proliferation), hepatic focal lesions (typically induced by hepatitis), arthritis (inhibition of fibrosis of affected joints), and AIDS associated sarcoma.

Accordingly, in one particularly beneficial further aspect of the invention, Sialokinins are prepared and administered to treat hyperproliferative cellular conditions associated with endolumenal wall injuries, such as related to damage resulting from endolumenal medical interventions. In a particular beneficial mode, such aspect is applied specifically to treat wall injury response to endolumenal implants such as stents. Still more particularly, the present embodiments prepare and administer sialokinins, and in particular SK1, to inhibit restenosis resulting from vascular stent implants in conjunction with balloon angioplasty.

Many different drugs, agents, and other treatment modalities such as radiation therapy have been disclosed in order to treat and prevent stenosis of a lumen vessel due to the lumenal response to injury. In particular, much has been investigated with respect to treating and preventing restenosis of vessels due to injury to the vessel wall, such as in response to angioplasty or restenosis.

Many such drugs and compounds that have been investigated for preventing restenosis have been disclosed in combination with stents, generally expandable cages or other mechanical scaffolding implanted within a vessel or other lumen to structurally engage or otherwise hold the corresponding lumenal wall open in order to keep the lumen patent.

Restenosis of a blood vessel, e.g. coronary or peripheral vessels, has been characterized as a cyclical cascade of events related to the injury, smooth muscle cell ("SMC") proliferation and migration. Drugs identified at preventing restenosis can be generally categorized in terms of their mode of treatment along the course of that cascade. In general, a first group of compounds are intended to treat the "medial proliferation" stage of the cascade, otherwise known as "anti-proliferative" compounds. A second group is intended to treat the "migration" stage, otherwise known as "anti-migratory" compounds. The SMC cell cycle as implicated in restenosis, including the intervening bioactivities of a variety of different types of "anti-restenosis" compounds, has been well characterized and the topic of many publications available to one of ordinary skill.

In addition, other compounds have been disclosed to prevent factors from instigating the SMC restenotic cycle, such as heparin or other compounds to prevent accumulation of factors associated with platelet or thrombus adhesion in the injured area (which has been observed to instigate the restenosis cycle). One example is a class of compounds generally considered to be "platelet aggregation inhibitors". A further example of a specific compound includes Heparin.

Compounds that have been investigated for their activity in the restenosis cycle can also be categorized by other means. Some compounds operate by virtue of their toxicity to the target tissue, essentially killing the tissue, often including the targeted tissue (e.g. SMC tissue) as well as other tissue (e.g. endothelium). Others are cytoskeletal inhibitors, inhibiting certain interactions between the cells and the matrix between them via the cellular skeletal wall. Others are believed to affect the internal function(s) of SMC's, such for example in order to prevent their reproductive activity (e.g. "anti-mitotic" compounds) or migratory activity. Still others are characterized by their vasodilatory action on the SMC tissue in the medial layer of the vessel, or "vasodilators", thus having anti-restenotic action by promoting relaxation and dilation of the overall vessel diameter (though this alone may often be only short-lived).

Other such compounds are "anti-inflammatory" compounds which inhibit the inflammatory response to the cell wall injury, such as infiltration of macrophages, etc. One example of an "anti inflammatory" compound being investigated for anti-restenosis activity is known as dexamethasone, which has been approved for use generally as an anti-inflammatory compound since 1952.

Still other such compounds are known as "matrix metalloproteinase (MMP) inhibitors", wherein MMPs (e.g. collagenases, stromelysins, and gelatinises) are enzymes believed to induce migration and proliferation of cells. One example of a MMP inhibitor is Batimastat being investigated by British Biotech.

Specific compounds may have only one of these characteristics in their bioactivity in relation to the restenosis cycle, or may have combinations of more than one anti-restenosis bioactivity.

Much research has been published about many of these drugs. On the forefront through clinical trials have been paclitaxel (e.g. Taxol™), Cisplatin™, and sirolimus (e.g. Rapamycin™). In particular, restenosis with stents coated with paclitaxel or rapamycin has been observed to drop below 10% of patients treated with respectively coated stents (e.g. investigations in clinical trials by Johnson & Johnson Corporation). However, Taxol™ and Cisplatin™ and rapamycin as well, have been observed in the past to cause toxicity in the area of treatment, preventing important healing in the area of treatment as undesirable "baggage" to the anti-restenosis action.

Other compounds that have been considered for restenosis also are believed to carry with them adverse affects such as tissue toxicity as well as their desired action to prevent restenosis. For example, certain foreign proteins as treatment compounds may be hystamines, or result in hystamine production at the target site, to thereby invoke an anti-hystamine response in the area of treatment that may be a negative side effect of any positive action that the protein may otherwise have for preventing restenosis.

It is believed that many if not all of the known compounds intended to prevent restenosis have significant side effects such as toxicity when dosed at levels sufficient to allow that compound, if used alone as the principal bioactive agent, to significantly prevent restenosis. Based upon recent published studies with known stent-compound combinations, "significant prevention" of restenosis is herein considered to be characterized by a restenosis outcome rate of generally below 10% of treated subjects based upon conventionally recognized standards such as measured cross-sectional lumenal diameter and/or measured flow rates across the treatment area. In particular, it is believed that dosages (e.g. amounts delivered over specified period of time) of any of the known anti-restenosis compounds alone (e.g. without other substantially active compounds for treating restenosis) sufficient to achieve <5% or close to or at 0% restenosis would generally result in unwanted toxicity or otherwise significant prevention of healing in the treated area.

One prior reference discloses a stent coated with at least one specific anti-restenosis compound in combination with an anti-inflammatory compound in order to prevent restenosis while remediating the otherwise inflammatory response that would occur with the therapeutic levels of the active compound.

Various different mechanisms have also been disclosed for delivering anti-restenosis compounds to vascular injury sites to prevent restenosis, including using local injection delivery (e.g. via needle balloon catheters), and more prominently coated stents. Various more particular mechanisms have been disclosed for coating stents, some of which are widely adapted for various types of compounds, while others are more particularly adapted to drug types, e.g. organic vs. inorganic, hydrophilic vs. hydrophobic, etc. Among the many disclosures, porous polymers are frequently investigated and described, such as PLGA, some of which incorporate multiple different polymer layers to achieve stent adhesion and controlled elution for the drug. Other disclosures include use of ceramic coating (e.g. aluminum oxide). Another disclosure includes the use of metal matrix co-deposited using electroless electrochemical deposition process together with a drug onto a metallic stent.

Further more detailed examples of compounds and related methods intended to inhibit restenosis response to vascular wall injury, or intended to provide a means for coating such compounds onto intralumenal stents, or provide other useful background with respect to other related aspects of the present invention, are variously disclosed in the following issued US patent References: U.S. Pat. Nos. 5,616,608 to Kinsella et al.; 5,624,411 to Tuch; 5,700,286 to Tartaglia et al.; 6,042,875 to Ding et al.; 6,143,037 to Goldstein et al.; 6,231,600 to Zhong; 6,258,121 to Yang et al.; 6,273,913 to Wright et al.; 6,280,411 to Lennox; 6,306,166 to Barry et al.; 6,309,380 to Larson et al.; 6,322,847 to Zhong et al. Further such examples are variously disclosed in the following published U.S. patent applications: US2001 00/32014 to Yang et al. Additional examples are variously disclosed in the following published PCT International Patent Applications: WO 95/03036 to Hunter et al.; WO 98/36784 to Ragheb et al.; WO 98/56312 to Wang et al.; WO 99/08729 to Barry et al.; WO 99/03517 to Dubois-Rande et al.; WO 99/21908 to Jackson et al.; WO 00/21584 to Barry; WO 00/27445 to Boock et al.; WO 00/32255 to Kamath et al.; WO 01/00667 to Valenzuela et al.; WO 01/01890 to Yang et al.; WO 01/87372 to Kopia et al. Still further examples are variously disclosed in the following published European Patents or Patent Applications: EP 0 568 310 to Mitchell et al.; EP 0 734 721 to Eury et al.; EP 0 747 069 to Fearnot et al.; EP 0 950 386 to Wright et al. The disclosures of these references are herein incorporated in their entirety by reference thereto.

Tachykinins are naturally occurring proteins that have been the topic of significant study and observation with respect to various of their observed bioactive properties, and in present day may also be readily synthesized as elsewhere herein described. In particular, salivary tachykinins, and in some cases more specifically mosquito salivary tachykinins, and in some cases still more specifically Sialokinins, have been observed to provide one or more of the following properties: vasodilation, antiproliferation, and platelet aggregation inhibition, as further developed below and elsewhere hereunder. However, tachykinins have yet to be recognized or adapted for beneficial therapeutic use, nor have they yet to be delivered to vascular injury sites to prevent restenosis, and in particular combining tachykinins, and in particular Sialokinins, with intralumenal stenting for the purpose of preventing or inhibiting restenosis.

Further more detailed examples of the observed bioactive properties of various tachykinins, and in certain cases more specifically Sialokinins, and which provide useful background information for a better general understanding of the present embodiments, are disclosed in various of the following references:

(1) Ribeiro, J. M. C., J. M. H. Hazzard, R. H. Nussenzveig, D. E. Champagne, and F. A. Walker, 1993 *"Reversible binding of nitric oxide by a salivary heme protein from a bloodsucking insect," Science* 260: 539-541;

(2) Champagne, D. E. and J. M. C. Ribeiro, 1994 *"Sialokinin I and II: Vasodilatory tachykinins from the yellow fever mosquito Aedes aegypti," Proceedings of the National Academy of Science U.S.A.* 91:138-142;

(3) Champagne, D. E. 1994, "The role of salivary vasodilators in bloodfeeding and parasite transmission," *Parasitology Today* 10: 430-433;

(4) Champagne, D. E., R. H. Nussenzveig, and J. M. C. Ribeiro, 1995, "Purification, partial characterization, and cloning of nitric oxide-carrying heme proteins (Nitrophorins) from salivary glands of the bloodsucking insect *Rhodnius prolixus*," *Journal of Biological Chemistry* 270: 8691-8695;

(5) Champagne, D. E., C. T. Smartt, A. A. James, and J. M. C. Ribeiro, 1995, *"The salivary gland-specific apyrase of the mosquito Aedes aegypti is a member of the* 5'-nucleotidase family," Proceedings of the National Academy of Science U.S.A. 92: 694-698;

(6) Francischetti I M, Ribeiro J M, Champagne D, Andersen J., 2000 "Purification, cloning, expression, and mechanism of action of a novel platelet aggregation inhibitor from the salivary gland of the blood sucking bug, Rhodnius prolixus," *Journal of Biological Chemistry*, 275:12639-50;

(7) Beerntsen B T, Champagne D E, Coleman J L, Campos Y A, James A A, "Characterization of the Sialokinin I gene encoding the salivary vasodilator of the yellow fever mosquito, *Aedes aegypti*," *Insect Mol. Biol.* 1999 8:459-67;

(8) Anderson J F, Weichsel A, Balfour C A, Champagne D E, Montfort W R, "The crystal structure of nitrophorin 5 at 1.5 A resolution: transport of nitric oxide by a lipocalin-based heme protein." *Structure* 1998 6:1315-27;

(9) Cupp M S, Ribeiro J M, Champagne D E, Cupp E W, "Analysis of cDNA and recombinant protein for a potent vasoactive protein in saliva of a blood-feeding black fly, *Simulium vittatum*," *J Exp Biol.* 1998 201:1553-61;

Weichsel A, Andersen J F, Champagne D E, Walker F A, Montfort W R, "*Crystal structures of a nitric oxide transport protein from a blood-sucking insect,*" *Nat Struct Biol.* 1998 5:304-9;

(10) Brown M R, Graf R, Swiderek K M, Fendley D, Stracker T H, Champagne D E, Lea A O, "*Identification of a steroidogenic neurohormone in female mosquitoes,*" *J Biol Chem* 1998 273:3967-71;

(11) Andersen J F, Champagne D E, Weichsel A, Ribeiro J M, Balfour C A, Dress V, Montfort W R, "Nitric Oxide binding and crystallization of recombinant nitrophorin I, a nitric oxide transport protein from the blood-sucking bug *Rhodnius prolixus*," *Biochemistry*, 1997 36:4423-8;

(12) Lundberg, Jan M. (1995) "*Tachykinins, sensory nerves, and asthma—an overview,*" *Canadian Journal of Physiological Pharmacology*, 73:908-914;

(13) Noveral, J. P. and M. M. Grumstein, "*Tachykinin regulation of airway smooth muscle cell proliferation,*" *Am. J. Physiol.*, 269:L339-343;

(14) Palma, C., M. Bigioni, C. Irrissuto, F. Nardelli, C. A. Maggi, and S. Manzini, "*Anti-tumour activity of tachykinin NK1 receptor antagonists on human glioma 0373 MG xenograft,*" *Brit. J. Cancer.*, 82:480-487;

(15) Reid, T. W., C. J. Murphy, C. K. Iwahashi, B. A. Foster, and M. J. Mannis, "*Stimulation of epithelial cell growth by the neuropeptide substance P,*" *J. Cell. Biochem.* 52:476-485.

The disclosures of each of these references provided in this list immediately above are herein incorporated in their entirety by reference thereto.

Accordingly, there is a need to prepare and apply tachykinins, and in particular Sialokinins, for treating restenosis.

There is also still a need for an anti-restenosis treatment that significantly prevents restenosis while allowing beneficial healing in the area of treatment.

Accordingly, a beneficial aspect of the invention provides an intralumenal stent that is has incorporated therewith a tachykinin, and more specifically Sialokinin, and still beneficially SK1, in a manner adapted to elute the tachykinin from the stent and into the vessel wall to inhibit restenosis there.

Sialokinins, and in particular SK1, are considered potent anti-restenosis agents, and in particular embodiments of the invention are used as a drug eluting stent coating, utilizing the various independent bioactivities elsewhere described herein that are consistent with anti-restenosis activity.

Restenosis is a condition wherein a vessel that is recanalized or opened during an intervention re-occludes, typically occurring within a 3 to 6 month time period. In response to balloon injury and stent implantation along a vessel wall, a vascular smooth muscle cell hyperproliferation condition often results and is considered a principle component of vascular restenosis. In general, pharmaceutical approaches that have been investigated as solutions to restenosis include intervening to the proliferation or mitosis of the smooth muscle cells, or promoting healing along the vascular wall lining (e.g. typically promoting endothelialization to repair an otherwise injured endothelial barrier to blood factors that stimulate SMC hyperproliferation), or both. A further condition associated with vascular restenosis is vascular "recoil", which is a mechanical response to the dilatation and consists of vascular wall contraction as a component to luminal reduction. Typical agents that have been investigated in the past with various degrees of success include anti-tumor agents, such as sirolimus (e.g. Rapamycin™) or paclitaxel (e.g. Taxol™), anti-inflammatory agents such as dexamethasone, and vasodilators such as nitric oxide (NO) (which has been observed to exhibit other properties believed to be useful in reducing vascular restenosis). In general, current trends are directed toward "cytostatic" approaches in lieu of "cytotoxic" approaches, as other harmful results of toxicity in vessel walls have been observed (e.g. negative remodeling or aneurysms).

SK1's observed bioactivity rendering it an appropriate anti-restenosis agent include: proven action on vascular endothelium as a stimulator of NO release and vasodilation, observed action in the inhibition of certain cellular immune responses (especially type 1 cytokine production), observed tumor inhibitory action in Lewis lung carcinoma mouse model, observed biocompatibility without toxicity in intravenous animal applications, and observed anti-proliferative bioactivity in human wart models.

Moreover, sialokinin has been observed to inhibit at least one bioactive molecule that has been further shown to provide a mechanism that instigates or otherwise promotes cellular migration. In the experimental Examples 1 and 2 provided elsewhere hereunder, less cancer cell migration, or "metasticizing," was observed in the Sialokinin test subjects when compared to positive (Cisplatin) and negative (Vehicle only) control groups. Accordingly, it is further believed, based upon observed experimental results and the further mechanistic understanding summarized above, that sialokinins may also provide helpful bioactivity as an anti-migratory agent in the restenosis inhibition process.

Sialokinin used according to the present embodiment is generally of the composition previously isolated and sequenced, as variously published, and is an organic peptide with a 10 amino acid sequence and a molecular mass of 1306 g/mol. Preparations for use in treating or preventing restenosis may include naturally (e.g. biologically) produced compound, or synthetically produced, or bioengineered production wherein cell cultures are modified to produce the peptide.

Previous studies observed sialokinin's principal biological activity as a vasodilator, a useful activity in preventing certain aspects of restenosis. This vasodilatory action of Sialokinin was shown to be dependent upon the presence of vascular endothelium and was stimulated by the release of NO in the vasculature as a result of sialokinin binding to the endothelium.

SK1 has furthermore been identified as a member of the tachykinin family with greatest sequence similarity to Substance P (SP). Binding to neurokinin receptors was proposed. As described previously, the neurokinin receptors are from a family of G protein-coupled receptors imbedded in the cell membrane of many types of cells in the mammalian body which act through phospholipase C and/or adenylate cyclase activation. Optimum dosage ranges for bioactivity of sialokinins have also been identified and are useful according to one of ordinary skill to achieve a desired dose for a particular restenosis application. More specifically, the optimum dosing concentration was shown to be 1-10 µM for bioactivity, with greater concentrations showing little benefit.

Further to sialokinin's inhibition of restenosis is the release of NO in the vasculature as a result of the sialokinin binding to vascular endothelium. In addition to vasodilatory effects, NO production or delivery in the vasculature has also been observed to inhibit vascular smooth muscle proliferation, platelet adhesion and aggregation, and local inflammation.

Further more detailed examples providing more detailed understanding of various aspects of NO bioactivity are disclosed in the following issued U.S. Pat. No. 6,087,479 to Stamler et al. The disclosure of this reference is herein incorporated in its entirety by reference thereto.

SK1 has been shown to inhibit certain cellular immune responses, another activity believed to be a valuable actor for inhibiting restenosis. For example, inhibition of cytokine production in mouse models has been observed. The suppression of type 1 immune responses (interleukin-2, interferon-α, and interferon-γ) has been observed as a significant aspect of the bioactivity. Type 2 responses (interleukin-4, interleukin-5, and interleukin-10) were also suppressed, though at a lower level to that observed for type 1. In a more specific example, spleen cell proliferation when stimulated with IL-2 in the presence of SK1 was suppressed by 66% and 39% in naïve and antigen activated cells, respectively. Spleen cell proliferation when stimulated with IL-4 in the presence of SK1 was also suppressed, but to a lesser degree—39% and 27% in naïve and antigen activated cells respectively. These tests were conducted with 25 µg/ml of salivary gland extract.

Other recent studies have implicated type 1 immune responses in the pathogenesis of arterial disease, implicating the observed bioactivity of SK1 as a related therapeutic agent.

The inhibition of negative cellular immune responses and proliferation in the vasculature post arterial trauma is significant in the inhibition of restenosis, and thus the present invention applying sialokinin as a restenosis agent is well supported by the previously observed bioactivity and experimental data for SK1 in relation to the common molecular biological actions being affected.

For example, in the study conducted with Lewis lung carcinoma in mice and elsewhere herein described, intratumor injections of sialokinins resulted in inhibition of tumor growth. Tumors larger than 100 mg received 50 µl injections. Greatest inhibition was shown with 5 and 10 µM dosing. The 5 µM test group showed 37, 36, and 16% tumor growth inhibition on day 7, 10, and 15, respectively. The 10 µM test group showed 38, 20, and 18% tumor growth inhibition on day 7, 10, and 15, respectively. For comparison, the study group dosed with Cisplatin showed 42, 7, and 27% tumor growth inhibition on day 7, 10, and 15, respectively. The 5 & 10 µM dosing equate to 0.5 ng/mg and 1 ng/mg of tissue respectively at 220 mg tumor size. Necropsy reports of the sialokinin test animals at 5, 10, and 100 µM dosing showed no detectable toxicity.

Necropsy reports of immuno-compromised mice which received 200 µl intravenous injection of 5 and 10 µM concentrations of SK1 showed no detectable toxicity or tissue necrosis. Because weight loss in study animals during or post dosing period is often considered a simple indication of toxicity, weight measurements were taken during the study period. No weight loss was detected in SK1 study group animals. Of note, the animals given Cisplatin experienced significant weight loss, and the comparison to the sialokinin test results leads to the reasonable inference that the sialokinins are less toxic than the Cisplatin in the respective doses delivered.

The anti-proliferative action of SK1 which is demonstrated in the local injection and systemic delivery tumor treatment examples, and the absence of detectable toxicity, are well correlated to applications for restenosis which implicates similar mechanisms.

In addition, according to the human efficacy trial for warts also elsewhere herein described, two 100 µl intra-tumor injections of 5 µM SK1 in clinically diagnosed stable and non-critical human warts larger than 50 mg showed bioactivity resulting in reduction in wart size. Size reductions of 19, 79, and 31% were observed in 3 of 4 subjects during the course of treatment. There was no measured or observed toxicity in trial subjects and no systemic symptoms were detected.

In the first clinical exposure for SK1, desired bioactivity in a human model was established and no side effects were detected. This trial also is significant in evaluating the potential of SK1 in treating restenosis.

This experience with anti-proliferative aspects of SK1 as demonstrated in the local injection wart treatment example is also well correlated to expected bioactivity in restenosis also sharing certain common features of unregulated cellular proliferation.

Further more detailed examples of tachykinins and various molecular biology aspects of such compounds, as well as related to certain particular cellular conditions, similar to those described variously above, are disclosed in the following background references: Champagne, D. E. and Ribeiro J. "Sialokinin I and II. Vasodilatory tachykinins from the yellow fever mosquito *Aedes aegypti.*" *Proc. Natl. Acad. Sci. USA* 1994; 91: 138-142; Cross, M. L., Cupp, E. W., and Enriquez, F. J. "Differential modulation of murine cellular immune responses by salivary gland extract of *Aedes aegypti.*" *Am. J. Trop. Med. Hyg.* 1994; 51(5): 690-696; Ribeiro, J. M. C. "Characterization of a vasodilator from the salivary gland of the yellow fever mosquito *Aedes aegypti.*" *J. Exp. Biol.* 1992; 165: 61-71; Ribeiro, J. M. C., Nussenzveig, R. H., and Tortorella, G. "Salivary vasodilators of *Aedes triseriatus* and *Anopheles gambiae* (Diptera: Culicidae)." *J. Med. Entomol.* 1994; 31(5): 747-753. The disclosures of these references are herein incorporated in their entirety by reference thereto.

It is to be appreciated that tachykinins may be delivered to endolumenal injury sites as anti-restenotic agents according to many different mechanisms, which are to be considered independently beneficial aspects of the present invention.

One highly beneficial aspect of the invention therefore is an intralumenal stent coated with a tachykinin or analog or derivative thereof. The tachykinin is adapted to be delivered from the stent into lumenal wall tissue in an area surrounding the stent at a dosage sufficient to inhibit a restenosis response to wall injury in the area.

In one mode of this aspect, the tachykinin comprises a sialokinin or analog or derivative thereof. In one embodiment, the sialokinin is a naturally occurring sialokinin. In another embodiment, the sialokinin is a synthesized molecule. In another embodiment, the sialokinin is produced biologically from a laboratory cell-culture that is bioengineered to produce the peptide. In another embodiment, the sialokinin is SK1.

In another regard, it is to be appreciated that the tachykinin may be coated onto the stent by securing it to the stent with a coating agent, or may be stored in a reservoir formed in or along the stent, or further more may be coated onto or incorporated into a graft or other covering or material structure associated with the stent. In one embodiment, a coating agent may be used that is a hydrophilic material. In another embodiment, the coating agent may be a hydrophobic material. In various beneficial embodiments, the coating agent is a porous material, wherein the tachykinin is adapted to be delivered into the surrounding tissue area through the pores of the porous material. Such may be for example a polymer material, or a combination of polymers, or may be other porous materials such as ceramic or metal matrix. In other embodiments, the coating agent may be a biodegradable or bioabsorbable material, wherein the tachykinin is adapted to be delivered into the surrounding tissue at a controlled rate over a prescribed period of time as the biodegradable or bioabsorbable material biodegrades or bioabsorbs, respectively, within the vessel. In another variation, a binding agent is secured to a metal wall of the stent, and the coating agent is secured to the binding agent and thereafter released at the vessel wall, such as by enzymatic cleaving or other activity experienced in the in-vivo environment.

As mentioned above, the tachykinin may also be coated onto the stent by providing at least one reservoir along at least one strut of the stent and loading the tachykinin into the reservoir. In further embodiments, the tachykinin may be stored in the reservoir in substantially dried, liquid, paste, or gel forms. In further embodiments, the tachykinin within the reservoir is combined with a delivery agent, which may be for example a binding agent, bioabsorbable material, or biodegradable material, or simply a vehicle to provide a combined solution that enhances delivery into the vessel wall.

Moreover, the tachykinin may be delivered in conjunction with a stent by providing a cover around an outer surface of the stent wall, or otherwise associated with the stent, and providing the tachykinin within or on the cover. In one variation, the cover comprises a bioabsorbable or biodegradable material, wherein the tachykinin is delivered into the surrounding area of tissue when the cover bioabsorbed or biodegrades, respectively. In another variation, the cover comprises a porous membrane, wherein the tachykinin is adapted to be delivered into the surrounding area of tissue through pores in the porous membrane. In another variation the cover comprises a cover wall and the tachykinin is contained within the cover wall, such as by adsorption or other mode of mixture or suspension within the material that forms the wall.

In various highly beneficial aspects, the tachykinin is, or is substantially similar to (with respect to bioactivity in the restenosis cycle) sialokinins from the yellow fever mosquito, *Aedes aegypti*, or analogs or derivatives thereof. However, tachykinins are not believed to heretofore been disclosed in conjunction with stenting or other endolumenal implants or recanalization procedures, and therefore such combinations should be construed broadly. In another aspect of the invention for example, the tachykinin delivered in conjunction with stenting or other endolumenal implants or recanalization procedures is, or has substantially similar biological activity to, tachykinin from the *Rhodnius prolixus* bug or analogs or derivatives thereof. In another aspect of the invention, the tachykinin delivered in conjunction with stenting or other endolumenal implants or recanalization procedures is, or has substantially similar biological activity to, tachykinin from the blood feeding black fly, *Simulium vittatum*, or analogs or derivatives thereof.

It is to be appreciated that the various restenosis aspects of the present invention are principally focused on use of tachykinins, more specifically sialokinins, and still more specifically SK1, from the yellow fever mosquito, *Aedes aegypti*. However, analogs or derivatives thereof are further contemplated, in particular to the extent exhibiting similar bioactivity with respect to restenosis. Moreover, it is to be appreciated that the disclosure herein related to combining tachykinin therapy with, in, or on stents, while highly beneficial, is illustrative of a broader aspect of the invention which combines tachykinins in general with stent and/or restenosis therapy. For example, further modifications contemplate incorporating other tachykinins with, in, or on stents, or otherwise incorporated into therapy or prophylaxis of restenosis or other conditions where benefits of the tachykinins may be gained by local elution. Examples of other tachykinins that may be included those from for example the *Rhodnius prolixus* bug, or the blood feeding black fly, *Simulium vittatum*, or analogs or derivatives thereof.

Accordingly, certain tachykinins provide useful bioactivity in conjunctive therapy as described, whereas others will be considered less or non-productive in such use. Thus, reference hereunder to "tachykinins" as a general class of compounds in reference to the various aspects, modes, and embodiments is intended to encompass those appropriately bioactive tachykinins, such as of the particular types herein identified or otherwise readily apparent by one of ordinary skill based upon this disclosure together with other available information in the art.

It is further contemplated that compounds herein disclosed may be delivered to a vascular site of injury either coated onto a stent, or also may be delivered separately than the stent, such as by local drug delivery or systemic delivery.

The present embodiments of the invention are particularly beneficial for treating coronary or peripheral vessel wall disorders, in particular relation to restenosis as related to stenting or other recanalization interventions. However, other lumenal or intercavitary wall injury disorders may be treated than vessel walls, or otherwise drug delivery may be beneficial through walls though not intended to particularly treat the walls. For example, vas deferens, bile duct, biliary duct, urethra, fallopian tubes, uterus, etc., are other representative lumens or body spaces where the various embodiments of the invention may be applied or modified suitably for use to treat conditions associated with those locations. Also, tachykinins as herein contemplated may also be prepared and applied to prevent formation of de novo lesions versus restenotic lesions, such as for example prophylactic delivery to a site believed to be at risk for stenosis such as sites identified as including vulnerable plaque.

Tachykinins, and in particular sialokinins, as herein described according to the various embodiments is generally considered a low molecular weight protein as a peptide, and therefore the various aspects of the inventions may be beneficially modified to incorporate other like peptides. Various contemplated modes for combining the tachykinin with stents, coatings, and other bioactive agents as provided above may be according to those modes previously disclosed in the art for securing and delivering other low molecular weight protein agents via implantable stents. Specific dosages, coating formulations, etc., may be adjusted for the appropriate stent structure upon which the tachykinin is to be placed (e.g. surface area changes per each stent design, and dosing may change accordingly), as well as with respect to the particular coating of choice (e.g. different coatings will hold different amounts and elute at different rates), as would be further developed by simple experimentation according to this disclosure. More specifically, prior experimentation with locally delivered SK1, in particular relation to cancerous tumors and warts, has produced preliminary efficacy and safety results at dosing ranges between about 5 & 10 μM, which equates to 0.5 ng/mg and 1 ng/mg tissue being treated, respectively (based upon delivery every other day over a treatment period). This may be used as a starting point for simple experimentation to achieve optimal dosing on particular stent/coating platforms.

For example, a review of publicly available literature provides certain correlations between tissue dosing and stent loading as relates to vascular stenting. In one particular example for illustration, at least one publication identified use of sirolimus in a combined polymer coating of PEVA and PBMA on a stent similarly designed to a "Bx-Velocity" model (commercially available from Cordis, a Johnson & Johnson company). Published literature provides sufficient information to correlate 140 micrograms of sirolimus on this stent to 3.9 nanograms delivery per milligram artery over a 30 day period.

This ratio of stent loading to tissue dosing may be used in conjunction with simple experimentation with a similar stent and coating to achieve the generally desired dosage of SK1 typically observed for safe and efficacious anti-proliferative treatments. For example, for one example of a desired vascular wall dose would equate to 1 ng/mg in the vessel wall if delivered every other day as done in other protocols and corresponding to the typically observed safety and efficacy for SK1 in other proliferating tissue types. A simple linear extrapolation of this provides 15 ng/mg tissue dosing over a 30 day period. Accordingly, one useful preparation for optimizing the anti-restenosis effects of SK1 in a similar coating and on a similar stent to the sirolimus model provides 15/3.9, or about 4 times, the amount of drug in the coating, or equivalent to about 560 micrograms on the stent. However, since coatings and pharmacokinetics behave differently with different compounds, the correlation between different drugs may not hold true and other preparations may be required for optimal results, as may be readily determined. For example, various different samples may be prepared to center around this point and tested in standard animal test models, such as in 28 day survival pig models. One example of such simple experiment provides five treatment groups of 280 (50% dose), 420 (75% dose), 560 (mean dose), 700 (125% dose), and 840 (150% dose) micrograms. Results according to this range of treatment groups would provide sufficient data to optimize the desired dose of the SK1 on that particular stent and coating platform. More over, for the purpose of further illustration, in order to achieve the lower dose of 0.5 ng/mg tissue also previously determined to be safe and efficacious in other varied hyperproliferative tissues, this simple experimentation could be performed along similar protocol with all doses halved. Even if none of the groups provided optimal results in either of these cases, trends in the data would generally provide the necessary information to further experimentation to converge into the optimal range.

For the purpose of further illustration with respect to the various stent embodiments provided hereunder, the following is a brief description of illustrative embodiments shown in FIGS. 4A-8.

FIGS. 4A-C show a vessel 2 with a lesion or occlusion 4 being recanalized by a drug eluting stent ("DES") system as follows. The DES system includes a stent delivery system 10 that is a catheter having at its distal end portion 12 an expandable balloon 20 coupled to a balloon expandable stent 30. At the opposite proximal end portion shown schematically in the figure is a coupler to couple to a balloon inflation source 50. The device shown is tracked over a guidewire 40, and is shown as a classic "over the wire" design but may otherwise be monorail or "rapid exchange" capable.

As further shown in FIG. 4B, guidewire 40 is used to cross lesion 4, over which balloon 20 and stent 30 are advanced across the lesion 4. The balloon expansion provides angioplasty dilation, as well as stent deployment. Upon subsequent deflation of balloon 20 and withdrawal of the delivery assembly, the deployed stent 30 engages the wall of vessel 2 along the lesion site 4 to provide a mechanical scaffolding to prop open the area for maintained blood flow. In this position, over time a combination of recoil and neointimal formation typically combine to re-occlude the vessel. While the stent scaffolding substantially prevents recoil, it is the drug elution of tachykinins, and more particularly sialokinins, that prevent or at least substantially inhibit the neointimal formation via the various mechanisms provided hereunder. In addition, certain vasodilatory effects of the tachykinin or sialokinin may further assist in the mechanically maintaining the patent lumen at desired open diameters.

Of the various modes for storing and eluting the tachykinins, certain particular embodiments are shown for illustration purposes in FIGS. 5 to 8. FIG. 5 shows an example of a drug eluting stent 60 structure with a strut 62 coated with a coating 64 that holds and elutes the sialokinin 66. In a modified DES version 70 shown in FIG. 6, stent strut 72 is coated with a first coating layer 74 and also a second coating layer 76. The first coating layer holds the tachykinin material 78, whereas the outer layer 76 aids in controlling elution at a desired rate, such as through specified porosity or permeability to the compound. FIG. 7 shows still further variation having a stent strut 80 with a cavity or channel 82 formed in the strut itself to hold the compound 88. Such reservoir may be partially into the stent strut, or may be completely formed therethrough, in which case a cover may be required to hold the material in without premature leakage. A further illustrative example shown in FIG. 8 shows a stent graft assembly 90 with adjacent struts 92,94 of a stent which are shown covered by a sheet or graft material 96 that holds the tachykinin material and elutes in-vivo for therapy.

It is to be appreciated that these examples just described by reference to the figures represent highly beneficial modes of the invention, which may be taken in combination or alternative to each other as apparent to one of ordinary skill. However, they are also considered illustrative of broader aspects of the invention and are not considered so limiting. For example, stents of the self-expanding type, e.g. constructed from shape-memory or superelastic metal alloy such as Nickel—titanium alloy may be used instead of a balloon expandable stent as shown in FIGS. 4A-C. Other coating elution modes may also be used, such as for example according to one or more references introduced herein and incorporated by reference.

The various aspects, modes, embodiments, variations, and features herein shown and/or described are to be considered independently beneficial. However, their various combinations are further contemplated within the intended scope of the invention as would be apparent to one of ordinary skill.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no ele ment, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

|  | Sequence |
|---|---|
| Sialokinin I SEQ. ID. NO. #1 (SK1) | Asn$^1$-Thr$^2$-Gly$^3$-Asp$^4$-Lys$^5$-Phe$^6$-Tyr$^7$-Gly$^8$-Leu$^9$-Met$^{10}$-NH2 |
| Sialokinin II SEQ. ID. NO. #2 (SK2) | Asp$^1$-Thr$^2$-Gly$^3$-Asp$^4$-Lys$^5$-Phe$^6$-Tyr$^7$-Gly$^8$-Leu$^9$-Met$^{10}$-NH2 |
| Substance P SEQ. ID. NO. #3 (SP) | Arg$^1$-Pro$^2$-Lys$^3$-Pro$^4$-Gln$^5$-Gln$^6$-Phe$^7$-Phe$^8$-Gly$^9$-Leu$^{10}$-Met$^{11}$-NH2 |
| Neurokinin A SEQ. ID. NO. #4 (NKA) | His$^1$-Lys$^2$-Thr$^3$-Asp$^4$-Ser$^5$-Phe$^6$-Val$^7$-Gly$^8$-Leu$^9$-Met$^{10}$-NH2 |
| Neurokinin B SEQ. ID. NO. #5 (NKB) | Asp$^1$-Met$^2$-His$^3$-Asp$^4$-Phe$^5$-Phe$^6$-Val$^7$-Gly$^8$-Leu$^9$-Met$^{10}$-NH2 |
| Neuropeptide K SEQ. ID. NO. #6 (NPK) | Asp$^1$-Ala$^2$-Asp$^3$-Ser$^4$-Ser$^5$-Ile$^6$-Glu$^7$-Lys$^8$-Gln$^9$-Val$^{10}$-Ile$^{11}$-Ser$^{12}$-His$^{13}$-Lys$^{14}$-Arg$^{15}$-Leu$^{16}$-Tyr$^{17}$-Gly$^{18}$-His$^{19}$-Gly$^{20}$-Gln$^{21}$-Gln$^{22}$-Ile$^{23}$-Ser$^{24}$-His$^{25}$-Lys$^{26}$-Arg$^{27}$-His$^{28}$-Lys$^{29}$-Thr$^{30}$-Asp$^{31}$-Ser$^{32}$-Phe$^{33}$-Val$^{34}$-Gly$^{35}$-Leu$^{36}$-Met$^{37}$-NH2 |
| Neuropeptide y SEQ. ID. NO. #7 (NP y) | Asp$^1$-Ala$^2$-Gly$^3$-His$^4$-Gly$^5$-Gln$^6$-Ile$^7$-Ser$^8$-Ser$^9$ Lys$^{10}$-Arg$^{11}$-His$^{12}$-Lys$^{13}$-Thr$^{14}$-Asp$^{15}$-Ser$^{16}$ Phe$^{17}$-Val$^{18}$-Gly$^{19}$-Leu$^{20}$-Met$^{21}$-NH2 |

Common amino acid residues with the Sialokinins are in bold type.

What is claimed is:

1. A method for treating a wart, comprising:
   delivering a therapeutic dose of material comprising a combination of SK1 and SK2 sialokinins to a wart.

2. The method of claim 1, wherein SK1 and SK2 sialokinins are present in the material at a ratio of about a 4:1.

3. The method of claim 1:
   wherein the therapeutic dose of material comprises delivering multiple bolus volumes of the material with a frequency over a duration that comprises a period of time for treatment; and
   wherein inhibition is achieved during the period of time.

4. The method of claim 1, where in the delivery of said therapeutic dose is performed by subcutaneous injections directly into a region of the wart.

5. The method of claim 1, wherein the therapeutic dose comprises between about 1 to about 10 nanomolar preparation of the sialokinin combination.

6. The method of claim 1, wherein the therapeutic dose comprises between about 0.5 to about 1 nanogram of sialokinin per millimeter of tissue being treated.

7. The method of claim 3, wherein the multiple bolus volumes are delivered locally into a region of a wart.

8. The method of claim 7, wherein the local delivery is performed via needle injection directly into the region of the wart.

9. The method of claim 3, wherein the bolus volumes are delivered via systemic delivery.

10. The method of claim 3, wherein the duration comprises more than one day.

11. The method of claim 10:
    wherein the therapeutic dose comprises between about 1 to about 7 nanograms of the sialokinin being delivered over the duration per milligram of tissue being treated.

12. The method of claim 10, wherein:
    the therapeutic dose comprises a daily average dose of that is between about 0.25 to about 0.5 nanogram of sialokinin per milligram tissue being treated per day over the duration.

* * * * *

SEQUENCE LISTING

<160> NUMBER OF SEQ ID NOS: 9

<210> SEQ ID NO 1
<211> LENGTH: 10
<212> TYPE: PRT
<213> ORGANISM: Aedes aegypti

<400> SEQUENCE: 1

Asn Thr Gly Asp Lys Phe Tyr Gly Leu Met
1               5                   10

<210> SEQ ID NO 2
<211> LENGTH: 10
<212> TYPE: PRT
<213> ORGANISM: Aedes aegypti

<400> SEQUENCE: 2

Asp Thr Gly Asp Lys Phe Tyr Gly Leu Met
1               5                   10

<210> SEQ ID NO 3
<211> LENGTH: 11
<212> TYPE: PRT
<213> ORGANISM: Homo sapiens

<400> SEQUENCE: 3

Arg Pro Lys Pro Gln Gln Phe Phe Gly Leu Met
1               5                   10

<210> SEQ ID NO 4
<211> LENGTH: 10

```
<212> TYPE: PRT
<213> ORGANISM: Homo sapien

<400> SEQUENCE: 4

His Lys Thr Asp Ser Phe Val Gly Leu Met
1               5                   10

<210> SEQ ID NO 5
<211> LENGTH: 10
<212> TYPE: PRT
<213> ORGANISM: Homo Sapien

<400> SEQUENCE: 5

Asp Met His Asp Phe Phe Val Gly Leu Met
1               5                   10

<210> SEQ ID NO 6
<211> LENGTH: 37
<212> TYPE: PRT
<213> ORGANISM: Homo sapien

<400> SEQUENCE: 6

Asp Ala Asp Ser Ser Ile Glu Lys Gln Val Ile Ser His Lys Arg Leu
1               5                   10                  15

Tyr Gly His Gly Gln Gln Ile Ser His Lys Arg His Lys Thr Asp Ser
            20                  25                  30

Phe Val Gly Leu Met
            35

<210> SEQ ID NO 7
<211> LENGTH: 21
<212> TYPE: PRT
<213> ORGANISM: Homo Sapien

<400> SEQUENCE: 7

Asp Ala Gly His Gly Gln Ile Ser Ser Lys Arg His Lys Thr Asp Ser
1               5                   10                  15

Phe Val Gly Leu Met
            20

<210> SEQ ID NO 8
<211> LENGTH: 7
<212> TYPE: PRT
<213> ORGANISM: Homo sapien
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 8

Xaa Xaa Phe Xaa Gly Leu Met
1               5

<210> SEQ ID NO 9
<211> LENGTH: 4
<212> TYPE: PRT
<213> ORGANISM: Homo Sapien

<400> SEQUENCE: 9

Arg Pro Lys Pro
1
```